(12) United States Patent
Jaworski et al.

(10) Patent No.: US 9,669,126 B2
(45) Date of Patent: Jun. 6, 2017

(54) VOLATILE MATERIAL DISPENSER AND METHOD OF EMITTING A VOLATILE MATERIAL

(71) Applicants: Thomas Jaworski, Kenosha, WI (US); Dennis J. Beaumont, Libertyville, IL (US); Scott D. Walter, Twin Lakes, WI (US)

(72) Inventors: Thomas Jaworski, Kenosha, WI (US); Dennis J. Beaumont, Libertyville, IL (US); Scott D. Walter, Twin Lakes, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 644 days.

(21) Appl. No.: 13/959,217

(22) Filed: Aug. 5, 2013

(65) Prior Publication Data
US 2014/0037273 A1 Feb. 6, 2014

Related U.S. Application Data

(60) Provisional application No. 61/680,110, filed on Aug. 6, 2012.

(51) Int. Cl.
*A61M 16/00* (2006.01)
*F24F 6/08* (2006.01)
*A61L 9/03* (2006.01)

(52) U.S. Cl.
CPC ......... *A61L 9/037* (2013.01); *A61L 2209/133* (2013.01); *A61L 2209/135* (2013.01)

(58) Field of Classification Search
None
See application file for complete search history.

(56) References Cited

U.S. PATENT DOCUMENTS

| | | | |
|---|---|---|---|
| 3,288,556 A | 11/1966 | Weber, III | |
| 4,251,714 A | 2/1981 | Zobele | |
| 4,771,563 A | 9/1988 | Easley | |
| 4,874,924 A | 10/1989 | Yamamoto et al. | |
| 5,038,394 A * | 8/1991 | Hasegawa ........... | A01M 1/2077 392/392 |

(Continued)

FOREIGN PATENT DOCUMENTS

| | | |
|---|---|---|
| EP | 1825748 A2 | 8/2007 |
| EP | 2468118 A1 | 6/2012 |

(Continued)

OTHER PUBLICATIONS

PCT/US2013/053700 International Search Report dated Nov. 7, 2013.

*Primary Examiner* — Thor Campbell

(57) ABSTRACT

A volatile material dispenser includes a housing having at least one wall and a cavity disposed within the housing and a refill having a volatile material therein and a wick in contact with the volatile material and extending out of the refill. The dispenser further includes a heater arrangement disposed within the cavity and surrounding the wick when the refill is inserted into the dispenser. The heater arrangement provides a reduced power consumption of at least about 30% as compared to other similar volatile material dispensers that have an average rate of weight loss that is similar to or less than the volatile material dispenser.

16 Claims, 27 Drawing Sheets

(56) References Cited

U.S. PATENT DOCUMENTS

| | | | |
|---|---|---|---|
| 5,222,186 A * | 6/1993 | Schimanski | A61L 9/03 392/392 |
| 5,402,517 A * | 3/1995 | Gillett | A01M 1/2077 261/DIG. 89 |
| 5,647,053 A | 7/1997 | Schroeder et al. | |
| 5,940,577 A | 8/1999 | Steinel | |
| 6,085,026 A * | 7/2000 | Hammons | A61L 9/03 219/544 |
| 6,141,496 A * | 10/2000 | Sundberg | A61L 9/03 392/390 |
| 6,236,807 B1 * | 5/2001 | Ruffolo | A61L 9/037 392/390 |
| 6,289,176 B1 * | 9/2001 | Martter | A61L 9/03 392/390 |
| 6,446,384 B2 | 9/2002 | Pedrotti et al. | |
| 6,487,367 B2 | 11/2002 | Vieira | |
| 6,501,906 B2 | 12/2002 | Vieira | |
| 6,563,091 B2 | 5/2003 | Vieira | |
| 6,580,875 B2 * | 6/2003 | Rymer | A61L 9/037 392/392 |
| 6,594,445 B2 | 7/2003 | Basaganas Millan | |
| 6,603,924 B2 * | 8/2003 | Brown | A61L 9/037 219/541 |
| 6,697,571 B2 * | 2/2004 | Triplett | A61L 9/03 392/395 |
| 6,782,194 B2 | 8/2004 | Schneiderbauer | |
| 6,859,615 B2 | 2/2005 | Yip et al. | |
| 6,909,840 B2 | 6/2005 | Harwig et al. | |
| 7,014,818 B2 | 3/2006 | Rymer | |
| 7,167,641 B2 | 1/2007 | Tam et al. | |
| 7,519,279 B2 | 4/2009 | Zobele | |
| 7,674,429 B2 * | 3/2010 | Lins | A01N 31/02 239/145 |
| 7,932,482 B2 * | 4/2011 | Norwood | A01M 1/2077 219/494 |
| 7,962,017 B2 | 6/2011 | Viera | |
| 8,983,279 B2 * | 3/2015 | Adair | A61L 9/037 239/136 |
| 2005/0069307 A1 * | 3/2005 | He | A01M 1/2072 392/395 |
| 2007/0237498 A1 * | 10/2007 | Helf | A01M 1/205 392/386 |
| 2013/0266297 A1 * | 10/2013 | Ihle | A01M 1/2077 392/386 |
| 2014/0037273 A1 * | 2/2014 | Jaworski | A61L 9/037 392/390 |

FOREIGN PATENT DOCUMENTS

| | | |
|---|---|---|
| WO | 2006026637 A2 | 3/2006 |
| WO | 2006105397 A1 | 10/2006 |
| WO | 2009044123 A1 | 4/2009 |
| WO | WO 2012/052321 A1 | 4/2012 |

* cited by examiner

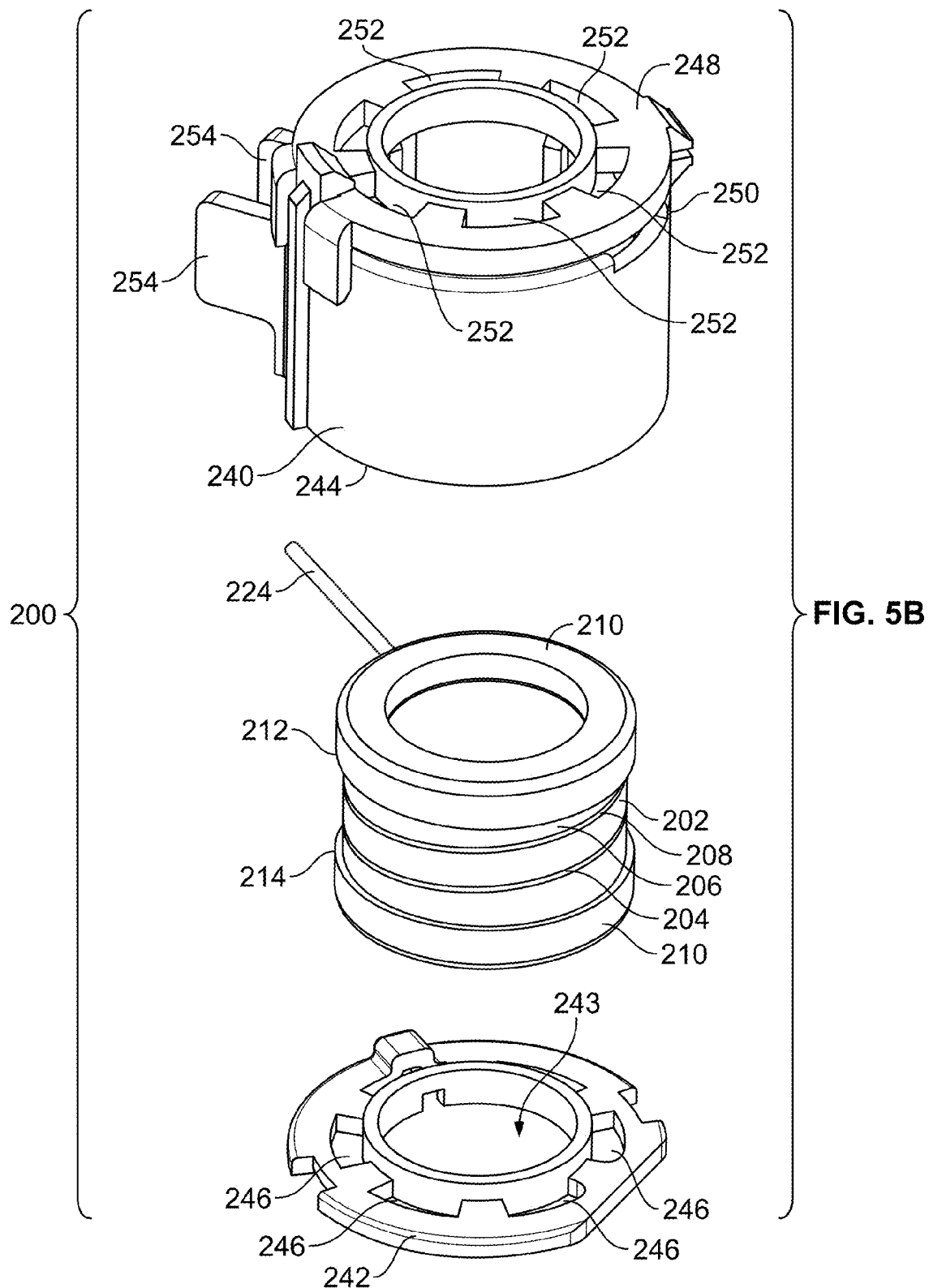

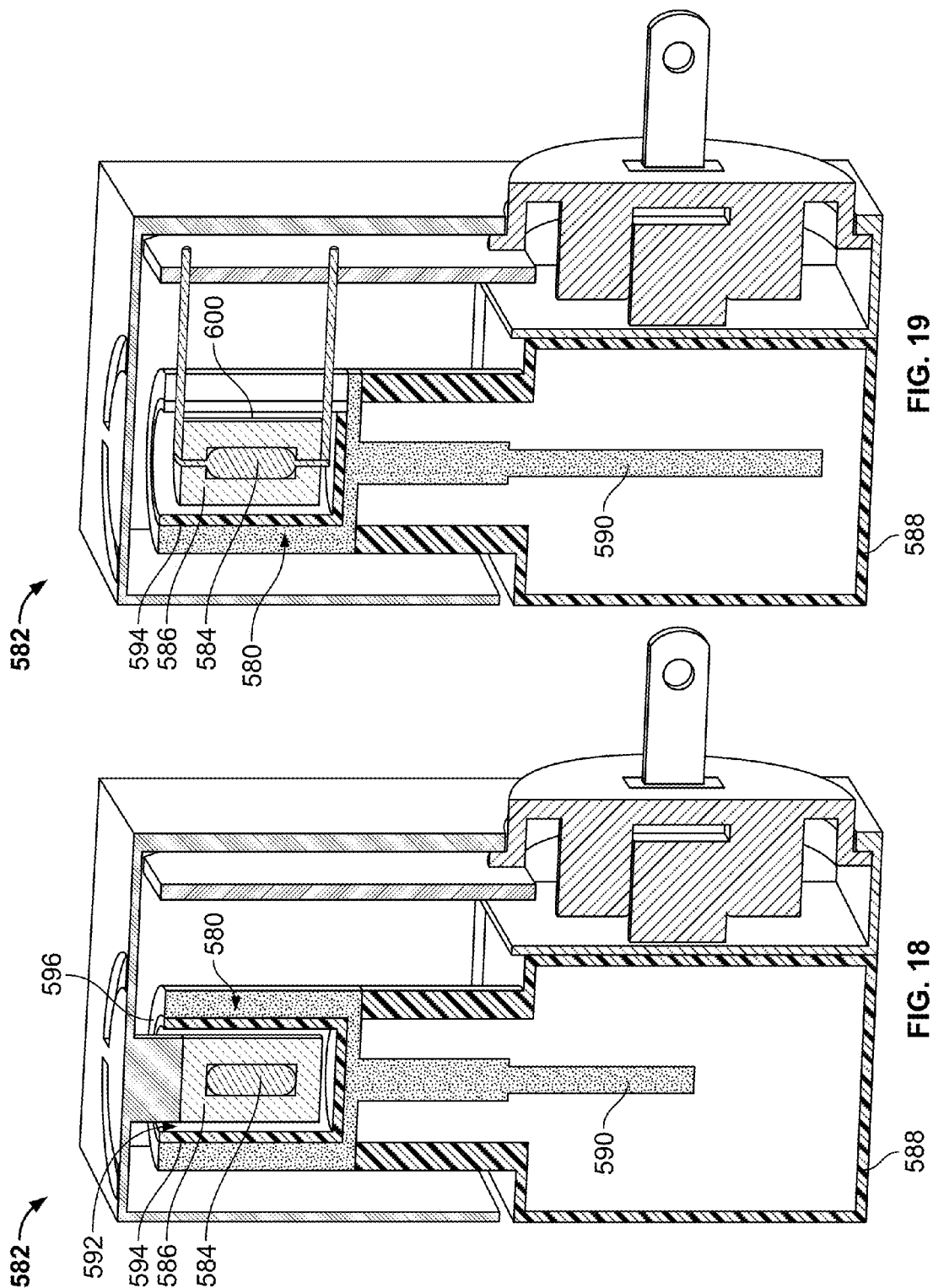

VOLATILE MATERIAL DISPENSER AND METHOD OF EMITTING A VOLATILE MATERIAL

CROSS REFERENCE TO RELATED APPLICATIONS

This application claims the benefit of Jaworski et al. U.S. Provisional Patent Application Ser. No. 61/680,110, filed on Aug. 6, 2012, and entitled "Volatile Material Dispenser".

BACKGROUND

1. Field of the Disclosure

The present invention relates generally to heaters for use in volatile material dispensers and, more particularly, to volatile material dispensers having heaters for volatilization of a volatile material.

2. Description of the Background

Various volatile material dispensers are known in the prior art and generally include a housing with a refill inserted therein. The refill generally includes a container for holding a volatile material therein. In some dispensers, the volatile material is passively emitted therefrom. In other dispensers, a diffusion element is utilized to facilitate the dispensing of the volatile material. Examples of diffusion elements include heaters, piezoelectric elements, fans, aerosol actuators, and the like. Regardless of the manner in which the volatile material is emitted, once the volatile material has been expended from the refill, the refill is removed by a user and replaced with a new refill.

One type of volatile material dispenser, which is sometimes referred to as a plug-in scented oil dispenser, includes a housing and a heater disposed within the housing. A refill for use with a plug-in scented oil dispenser generally includes a container with a volatile material therein and a wick in contact with the volatile material and extending out of the refill. Upon insertion of the refill into the dispenser, at least a portion of the wick is disposed adjacent the heater such that volatile material that moves through the wick is volatilized by the heater. The volatile material dispenser typically includes a plug assembly having electrical prongs extending outwardly from the housing. The electrical prongs are inserted into a standard electrical outlet and thereafter supply electrical energy to the volatile material dispenser. Plug-in scented oil dispensers may also utilize a fan to aid in vaporizing and dispersing volatile material.

SUMMARY

In illustrative embodiments, a volatile material dispenser includes a housing having at least one wall and a cavity disposed within the housing and a refill having a volatile material therein and a wick in contact with the volatile material and extending out of the refill. The dispenser further includes a heater arrangement disposed within the cavity and surrounding the wick when the refill is inserted into the dispenser. The heater arrangement provides a reduced power consumption of at least about 30% as compared to other similar volatile material dispensers that have an average rate of weight loss that is similar to or less than the volatile material dispenser.

In other illustrative embodiments, a volatile material dispenser includes a housing having at least one wall and a cavity disposed within the housing and a refill having a volatile material therein and a wick in contact with the volatile material and extending out of the refill. The dispenser further includes a heater arrangement disposed within the cavity and disposed adjacent the wick when the refill is inserted into the dispenser, wherein the heater arrangement has an efficiency factor of greater than or equal to about 13.

In further illustrative embodiments, a method of emitting a volatile material includes the step of providing a volatile material dispenser having least one wall and a cavity disposed within the housing, wherein the housing accommodates a refill having a volatile material and a wick in contact with the volatile material and extending out of the refill. The method further includes the step of positioning a heater arrangement within the dispenser, wherein the heater arrangement is configured to reduce the power necessary to operate the dispenser. Still further, the method includes the step of operating the heater arrangement at a power of less than or equal to about 1.5 watts to achieve an average weight loss of at least 0.01 grams per hour.

BRIEF DESCRIPTION OF THE DRAWINGS

FIG. 5B is an exploded view of the heater arrangement of the dispenser of FIGS. 1-5A;

FIG. 14 is an exploded view of the heater and adjustment mechanism depicted in

FIG. 13;

FIGS. 17-25 depict enhancements that may be included within the heaters or heater arrangements of FIGS. 1-16;

Other aspects and advantages of the present invention will become apparent upon consideration of the following detailed description, wherein similar structures have like or similar reference numerals.

DETAILED DESCRIPTION

The present disclosure is directed to energy efficient heater arrangements for volatile material dispensers. While the present invention may be embodied in many different forms, several specific embodiments are discussed herein with the understanding that the present invention is to be considered only as an exemplification of the principles of the invention, and it is not intended to limit the invention to the embodiments illustrated.

Figure 1:
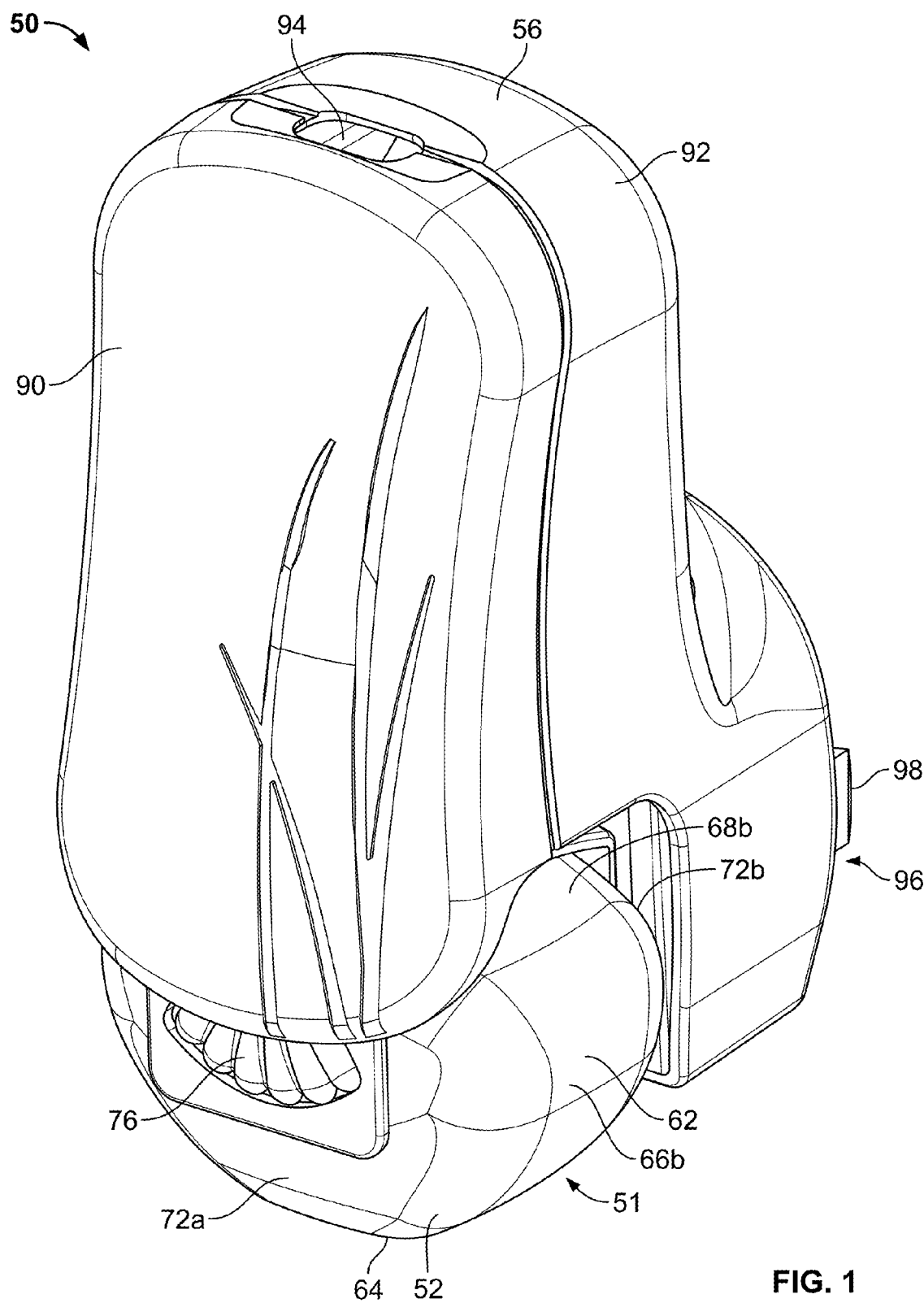
FIG. 1 is a top isometric view of a first embodiment of a volatile material dispenser employing an energy efficient heater arrangement.
Figure 2:
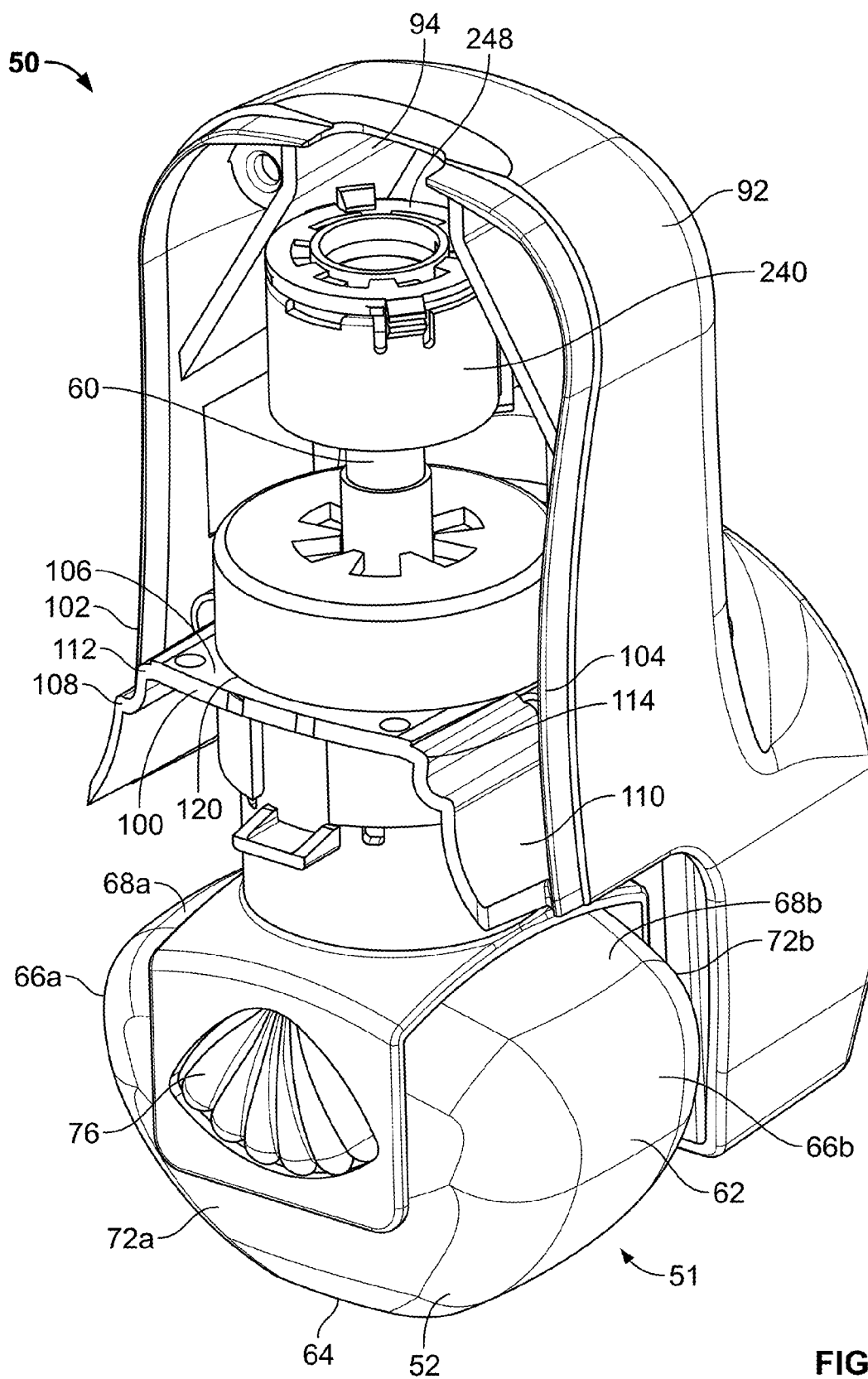
FIG. 2 is a top isometric view of the volatile material dispenser of FIG. 1 with a front portion of a housing removed therefrom to depict an interior cavity of the dispenser.

Referring to the drawings, FIGS. 1-5 depict a first embodiment of a volatile material dispenser 50 adapted to accommodate a refill 51, as seen in FIGS. 1 and 2, including a container 52 with a volatile material therein, wherein the container 52 is adapted to be retained by a housing 56. The container 52 includes a retaining mechanism 54 (see FIG. 9) to hold a wick 60 within the container 52 and a body 62 with the volatile material disposed therein. The body 62 includes a base portion 64 and first and second opposing sidewalls 66a, 66b that extend upwardly and outwardly prior to curving inwardly toward first and second top walls 68a, 68b, respectively. The first and second top walls 68a, 68b are integral with a neck 70 (see FIG. 9). Similarly, opposing front and rear walls 72a, 72b, respectively, curve upwardly toward the neck 70.

The neck 70 of the refill 51 includes a threaded portion disposed on an outer surface thereof and an opening 73 disposed through a top portion thereof, wherein the opening allows access to the volatile material. The retaining mechanism 54 is disposed within the neck 70 and further includes a sheath 75 that extends around at least a portion of the wick 60 to protect same. The container 52 further optionally includes raised portions 76 extending outwardly from one or more of the opposing front and rear walls 72a, 72b. In one embodiment, the raised portions 76 are in the form of inverted shell-shaped members. Although a specific dispenser 50 and container 52 are described with particularity, it is contemplated the heater arrangements of the present invention may be utilized in conjunction with any type of electrical dispenser employing a heater and any type of refill and/or container. For example, dispensers useful for the present invention include, but are not limited to, the dispensers described in Belongia et al. U.S. Pat. No. 7,840,123, Varanasi et al. U.S. Pat. No. 6,968,124, Beland et al. U.S. Patent Application Publication No. 2011/0049259, Zobele U.S. Patent Application Publication No. 2005/0180736, and Pedrotti et al. U.S. Pat. No. 6,862,403. Further, containers useful for the present invention include, but are not limited to, the containers described in U.S. Pat. No. 7,032,831, and the containers described in U.S. patent application Ser. No. 12/969,261, filed on Dec. 15, 2010, both of which are owned by the same assignee as the present invention.

The volatile material disposed in the container 52 may be any type of volatile material adapted to be dispensed into an environment. For example, the container 52 may include a cleaner, an insecticide, an insect repellant, an insect attractant, a disinfectant, a mold or mildew inhibitor, a fragrance, a disinfectant, an air purifier, an aromatherapy scent, an antiseptic, an odor eliminator, a positive fragrancing volatile material, an air-freshener, a deodorizer, or the like, and combinations thereof. Additives may be included in the volatile material, such as, for example, fragrances and/or preservatives.

Now turning generally to FIGS. 1-5, the housing 56 of the volatile material dispenser 50 generally includes front and rear portions 90, 92 attached to one another to form an interior chamber or cavity 93 therebetween. The front and rear portions 90, 92 also join to form an aperture 94 at a top of the housing 56 for the emission of volatile material therethrough. The refill 51 is inserted into the housing 56 by inserting the wick 60 upwardly into the chamber 93. Referring to FIGS. 1 and 5, a plug assembly 96 extends from the rear portion 92 of the housing 56 and includes two electrical prongs 98 adapted for insertion into a conventional outlet. While the plug assembly 96 is shown as being a convention plug assembly for the United States, a plug assembly adapted for use in any other country may be utilized. In addition, the plug assembly 96 may include any features known in the art, for example, the plug assembly 96 may be partially or fully rotatable.

While not depicted in the figures of the present application, the dispenser 50 may include a faceplate that is rotatably attached thereto, for example, as described in detail in Belongia et al. U.S. Publication No. 2012-0275772.

Figure 3:
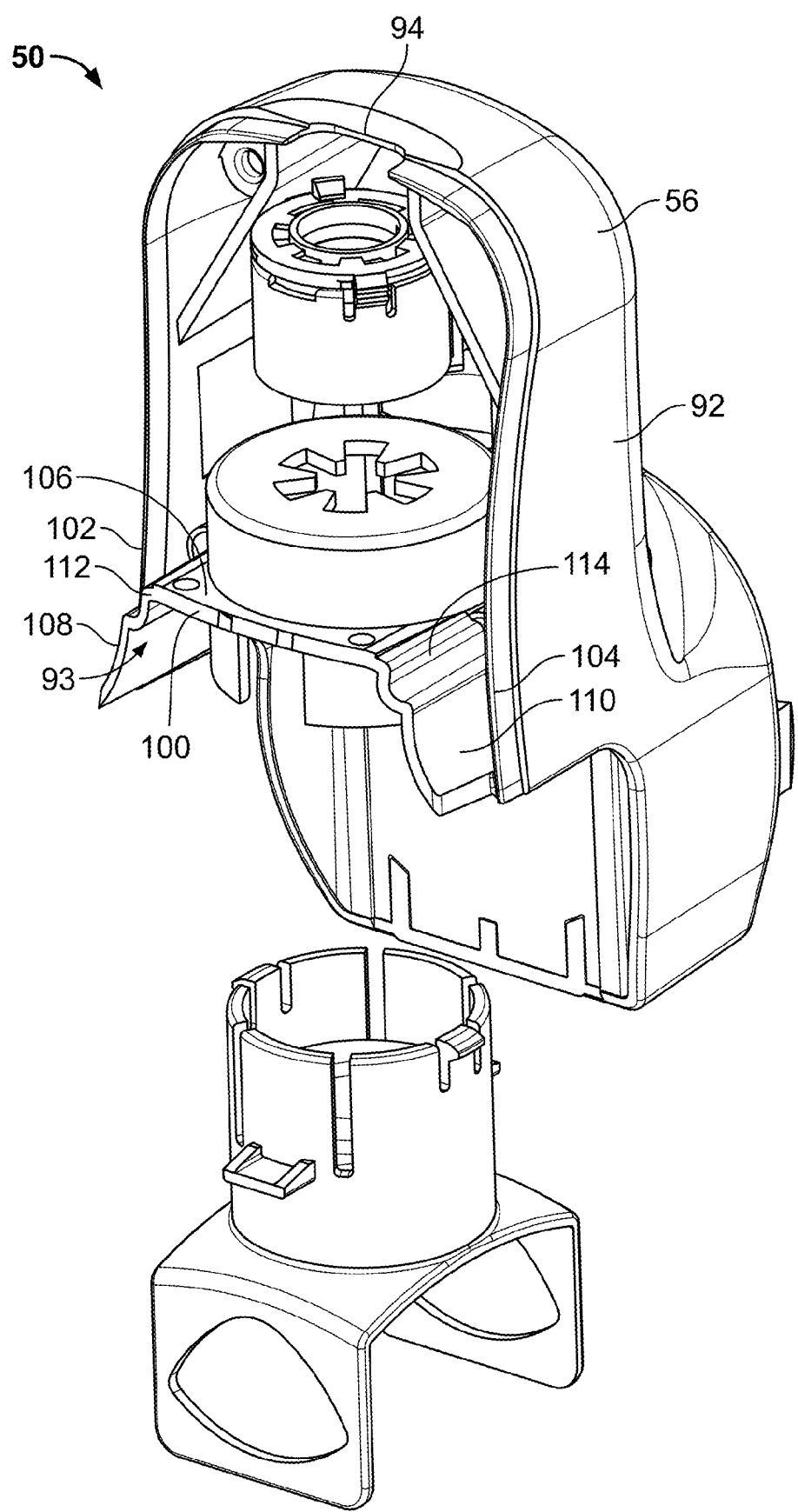
FIG. 3 is a top isometric, partial exploded view of the volatile material dispenser of FIG. 1 with the front portion of the housing removed therefrom and illustrating an adjustment mechanism for allowing adjustment of a refill disposed within the volatile material dispenser.

As best seen in FIGS. 2 and 3, a stationary support 100 is disposed within the housing 56 and extends between first and second sides 102, 104 of the housing 56. The support 100 includes a generally planar wall 106 and first and second arms 108, 110 extending downwardly and outwardly from opposite ends 112, 114, respectively, of the planar wall 106 to the first and second sides 102, 104. The arms 108, 110 are integral with or otherwise connected to the first and second sides 102, 104 of the housing 56.

Adjustment Mechanism

Figure 4:
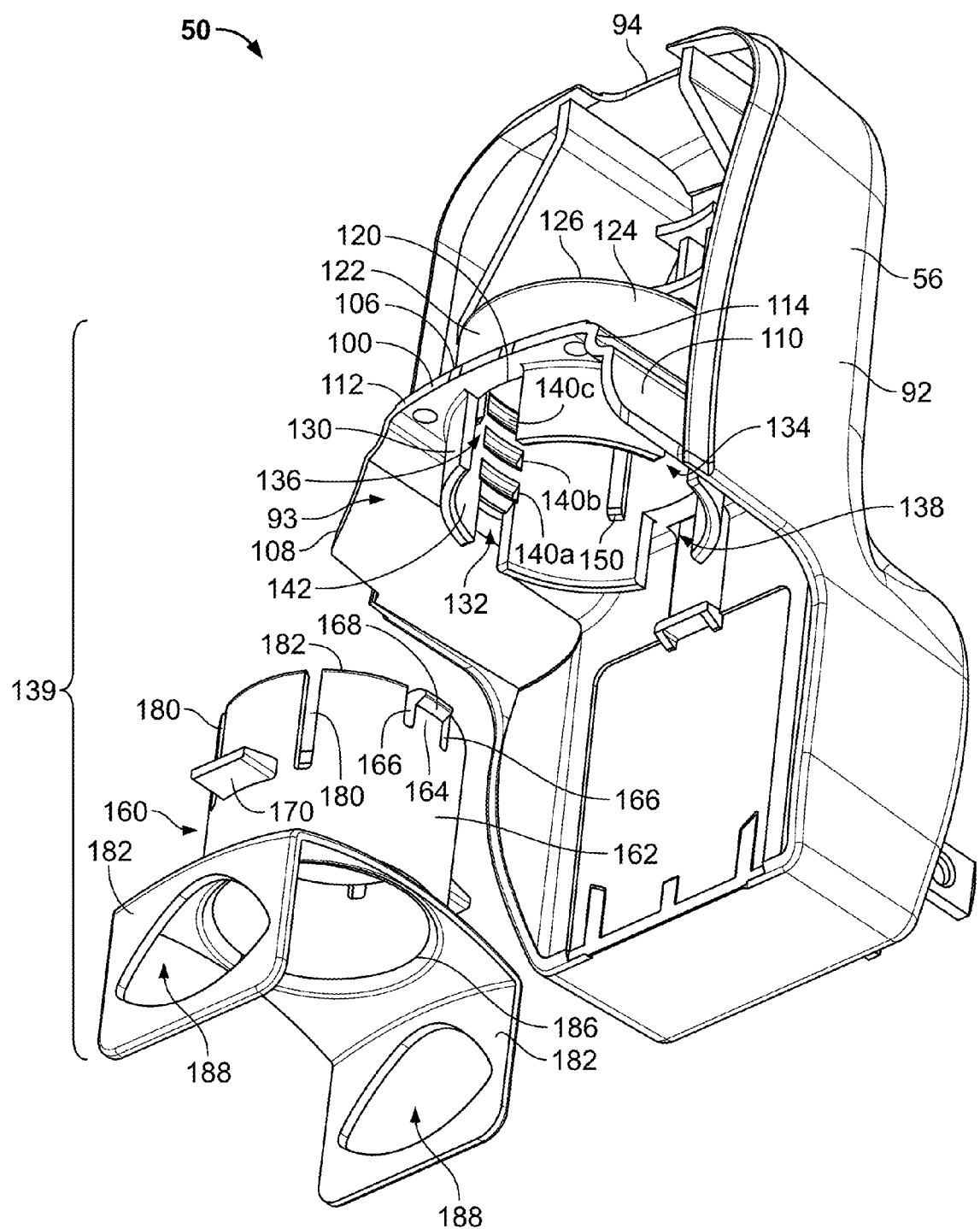
FIG. 4 is a bottom isometric, partial exploded view of the volatile material dispenser of FIG. 1 with the front portion of the housing removed therefrom and illustrating the adjustment mechanism.
Figure 5A:
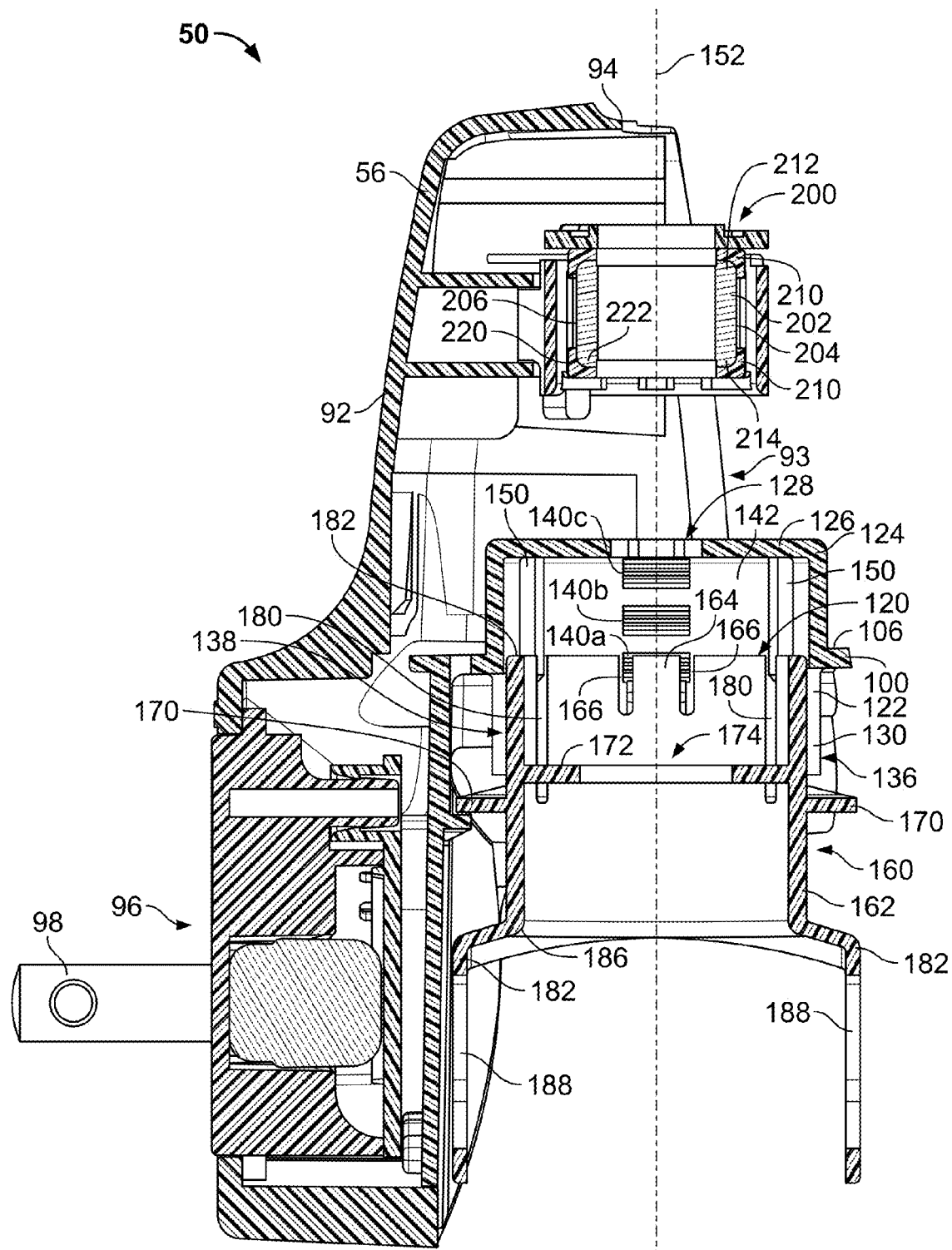
FIG. 5A is a cross-sectional view taken generally along the lines 5-5 of FIG. 2 and generally depicting a heater and an adjustment mechanism for moving the refill.

Referring to FIGS. 4 and 5A, the planar wall 106 of the support 100 includes a circular aperture 120 therethrough, wherein a cylindrical member 122 is formed within the circular apertures 120. The cylindrical member 122 includes an upper section 124 that extends above the planar wall 106 and is partially enclosed by a cover 126 with an aperture 128 for the wick 60, as will be discussed in greater detail below. The cylindrical member 122 further includes a lower section 130 that extends below the planar wall 106 and includes first and second opposing channels 132, 134 formed within sides of the lower section 130 and extending to the planar wall 106. The cylindrical member 122 further includes third and fourth opposing channels 136, 138 formed within front and rear sides of the lower section 130 and extending to planar wall 106. A first part of an adjustment mechanism 139 includes three sets of notches 140a-140c disposed in an inner surface 142 of the cylindrical member 122 in the upper and lower sections 124, 130. In particular, as seen in FIG. 5, a first of the sets of notches 140a is disposed within the lower section 130 above the third and fourth opposing channels 136, 138. Second and third sets of notches 140b, 140c are disposed within the upper section 124 above the first set of notches 140a. The function of the notches will be discussed in greater detail hereinafter.

Four elongate guide posts 150 extend outwardly from the upper section 124 of the cylindrical member 122, as seen in FIGS. 4 and 5, and are generally parallel to a longitudinal axis 152 (see FIG. 5A) of the dispenser 50. A guide post 150 is disposed between each adjacent channel 132, 134, 136, 138. While four guide posts 150 are depicted, any number of guide posts 150 that accomplish the function of guiding, as will be discussed below, may be utilized.

The adjustment mechanism 139 further includes a refill holder 160, as best seen in FIGS. 3-5A. The refill holder 160 includes a cylinder 162 adapted for insertion into the cylindrical member 122 of the support 100, as will be discussed in greater detail below. First and second flexible tabs 164 are disposed on opposite sides of the cylinder 162. The tabs 164 are formed by channels 166 in the cylinder 162 and further include outwardly extending projections 168. First and second rigid projections 170 extend outwardly from front and rear sides of the cylinder 162. The refill holder 160 further includes an annular ledge 172 (see FIG. 5A) that creates a generally planar surface and includes an aperture 174 therethrough. The wick 60 of the refill 51 may be inserted through the aperture 174, but the annular ledge 172 prevents over-insertion of the refill 51 into the dispenser 50.

Still referring to FIGS. 3-5, the cylinder 162 includes four elongate channels 180 extending downwardly from a top edge 182 of the cylinder 162 and generally parallel to the longitudinal axis 152 of the dispenser 50. One elongate channel 180 is disposed between each tab 164 and an adjacent rigid projection 170.

As seen in FIGS. 3-5, the refill holder 160 further includes two arms 182 extending outwardly and downwardly from front and rear sides of a lower edge 186 of the cylinder 162. Each arm 182 includes an aperture 188, respectively, therethrough. The apertures 188 may be formed in a shape that conforms to the raised portions 76 on the refill 51. The apertures 188 may optionally be any shape that would aid in retaining a refill 51 therein. Still optionally, the arms 182 and/or refill 51 may include any features that aids in attaching and retaining the refill 51 to the arms 182.

The adjustment mechanism 139 is assembled by inserting the cylinder 162 of the refill holder 160 into the lower section 130 of the cylindrical member 122 of the support 100. In this manner, the first and second flexible tabs 164 of the cylinder 162 are aligned within the first and second opposing channels 132, 134 in the side of the lower section 130 and the rigid projections 170 are aligned within the third and fourth opposing channels 136, 138 in the front and rear side of the lower section 130. At the same time, as best seen in FIG. 5A, the four elongate guide posts 150 on the upper section 124 of the cylindrical member 122 are aligned within the four elongate channels 180 extending outwardly from the cylinder 162. Each of these features acts to guide the refill holder 60 within the cylindrical member 122.

Once aligned, the refill holder 160 is pushed into the cylindrical member 122 until the projections 168 extending outwardly from the tabs 164 are disposed within the first set of notches 140a. The steps of assembling the adjustment mechanism 139 may be performed during manufacture and prior to purchase by a consumer or may optionally be performed by the consumer. Optionally, one or more features may be included to prevent withdrawal of the refill holder 160 from the cylindrical member 122 assembling.

During use of the dispenser 50, a user may desire a higher or lower emission of volatile material. The refill holder 160 may therefore be moved up and down to provide different levels of emission. In particular, when the projections 168 are disposed within the first set of notches 140a, the wick 60 is partially disposed within the heater 202, thereby providing a lower level of emission. Movement of the refill holder 160 such that the projections 168 are disposed within the second set of notches 140b moves the refill 51 upwardly, thereby moving the wick 60 farther into the heater 202. A highest level of emission is provided by moving the projections 168 into the third set of notches 140c. As can be understood by one skilled in the art, a user must change the intensity level of the dispenser 50. The intensity level is controlled by moving the refill holder 160 (and thus the position of the refill 51 and the wick 60) toward and away from the heater 202.

Heater Arrangement

Figure 15:
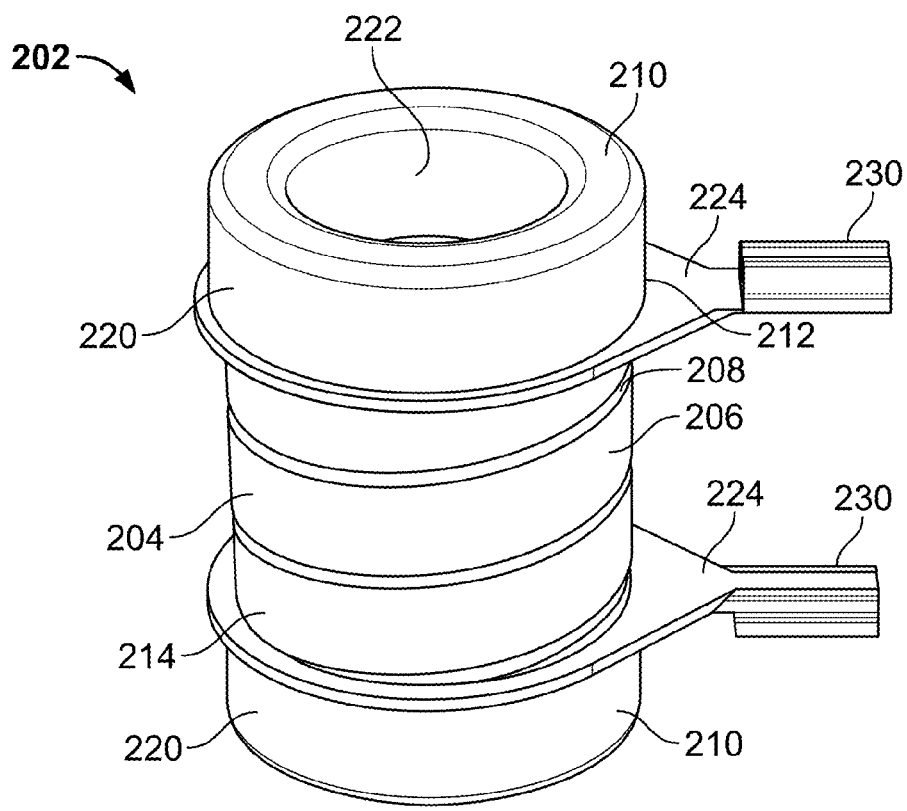
FIG. 15 is a first embodiment of a heater that may be used in conjunction with the embodiments of FIGS. 1-14.
Figure 16:
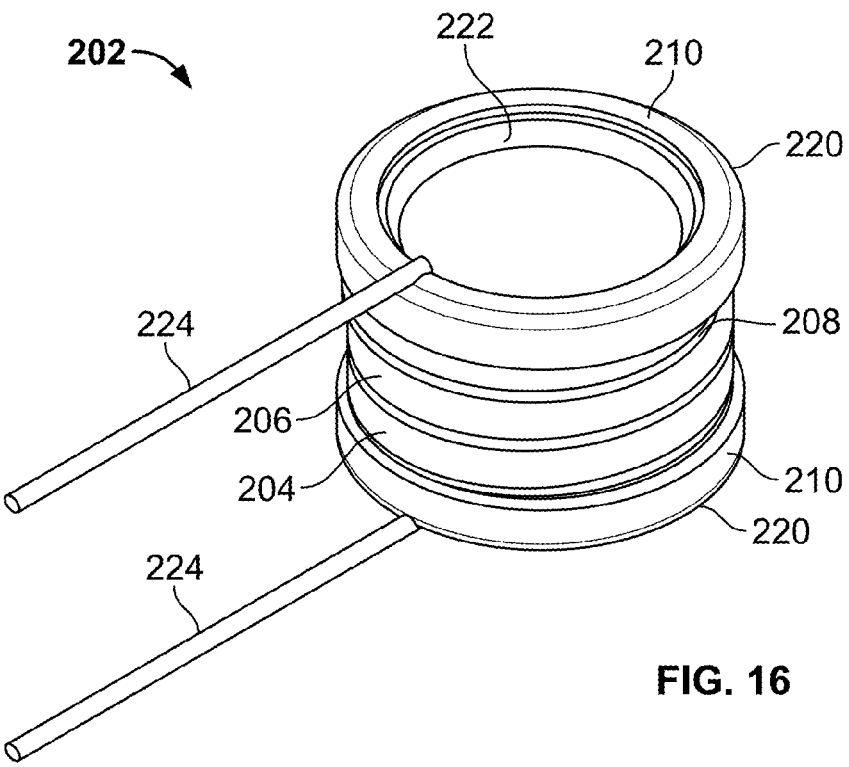
FIG. 16 is a second embodiment of a heater that may be used in conjunction with the embodiments of FIGS. 1-14.

Referring now to FIGS. 2, 3, 5A, and 5B, the dispenser 50 further includes a first embodiment of a heater arrangement 200 employing a heater or resistor 202. As seen in FIGS. 15 and 16, which depict two variations of the heater 202, the heater 202 in the form of a resistor includes a hollow ceramic cylinder 204 with a resistive metal oxide coating 206 that is deposited by sputter coating or spray coating on the hollow ceramic cylinder 204. A spiral pattern 208 may be formed in the resistive metal oxide coating 206 to create a desired resistance value for the heater 202. Alternatively, the ceramic cylinder 204 may be coated with a metal oxide coating 206 having a precise resistance value, thereby eliminating the need for spiral cutting. Metal end caps 210 are press fit onto first and second ends 212, 214 of the hollow ceramic cylinder 204. The metal ends caps 210 include caps 220 including a hollow cylindrical cavity 222 and one or more connectors 224 integral with or connected to the caps 210. The caps 210 fit over the ends 212, 214 of the cylinder 204 and the connector 224 extends around and away from the cylinder 204 and may terminate in terminals 230 (see FIG. 15), wherein either the connector(s) 224 or terminals 230 connect to a plug, circuit board, and/or other electrical components of the volatile material dispenser 50. The heater 202 may be coated with an insulating, dielectric, and/or flame resistant material or may be potted into a ceramic or plastic block. In one embodiment, the resistor 202 has a nominal resistance of between about 14 and about 16 Kohms with a 5% tolerance, a maximum rated power of about 3 Watts, and an operating voltage of between about 100 volts and about 230 volts. While a ceramic tube is disclosed, a wire may be wound into a tube to create the heater.

While FIGS. 15 and 16 are described as being a ceramic cylinder coated in a resistive metal oxide, the ceramic cylinder may optionally be coated with a carbon film, a resistive metal film, or a positive temperature coefficient (PTC) type material. In other illustrative embodiments, the cylinder may be wrapped with a resistive wire or flexible heating element. In still further illustrative embodiments, the cylinder may be formed of a PTC thermistor material (rather than a coated ceramic). In still further illustrative embodiments, a plurality of resistors or PTC thermistors may be arranged in a tubular arrangement or within a tubular structure to form a tubular heating arrangement. In still alternative illustrative embodiments, two or more of the heaters depicted in FIGS. 15 and 16 may be utilized. In illustrative embodiments, two or more heaters are stacked in a vertical fashion and a wick of a refill is inserted through the two or more heaters. In this manner, one or more of the heaters, which may be operated independently, may be operated at any point in time. In an illustrative embodiment in which two heaters are stacked, a first heater having a first resistance may be actuated for a low level of heat, a second heater having a second resistance greater than the first resistance may be actuated for a medium level of heat, and both heaters may be actuated for a high level of heat. Optionally, multiple resistors may be formed on a single ceramic tube to create the same effect. It should be understood that any combination of heaters, resistance levels, and/or levels of heat are within the scope of the present application. In still alternative embodiments, two or more heaters or heater arrangements may be associated with two or more different refills to provide for multi-fragrancing.

As best seen in FIG. 5B, the heater 202 may be disposed within a cylindrical container 240. The container 240 includes a lower plate 242 that is snap fit or otherwise attached to a lower end 244 of the container 240. The lower plate 242 includes a central aperture 243 and may include a plurality of auxiliary apertures 246 for migration of heat from the heater 202 therethrough. An upper plate 248 is snap fit or otherwise attached to an upper end 250 of the container 240 to, with the lower plate 242, enclose the heater 202 within the container 240. The upper plate 248 includes a central aperture 250 and may include one or more auxiliary apertures 252 for migration of heat therethrough. A side of the container 240 includes one or more apertures to accommodate the connectors 224 extending from the heater 202. The container 240 further includes at least one post 254 or other support to attach the heater to the housing 56.

A gap may be disposed between an outer periphery or outer diameter of the wick 60 and an inner periphery or inner diameter of the heater 200 or the cylindrical container 240 that may hold the heater 200. The gap should be large enough to allow sufficient airflow through the heater 200 or the heater arrangement 202, but small enough to provide sufficient heat transfer to the wick 60. In illustrative embodiments, the gap is between about 0.5 millimeter and 2.5 millimeters. In alternative illustrative embodiments, the gap is between about 1.0 millimeter and about 2.0 millimeters. In yet other illustrative embodiments, the gap is about 1.0 millimeter or about 1.5 millimeters.

Referring to FIG. 2, a refill 51 is inserted into the housing 56 by positioning the wick 60 within the cylinder 162 of the refill holder 160 and guiding the wick 60 through the cylindrical member 122 of the support member 100 and further through the central aperture 243 in the lower plate 242. In this manner, a portion of the wick 60 is disposed within a cylindrical core of the heater 202.

Experiment

Figure 26:
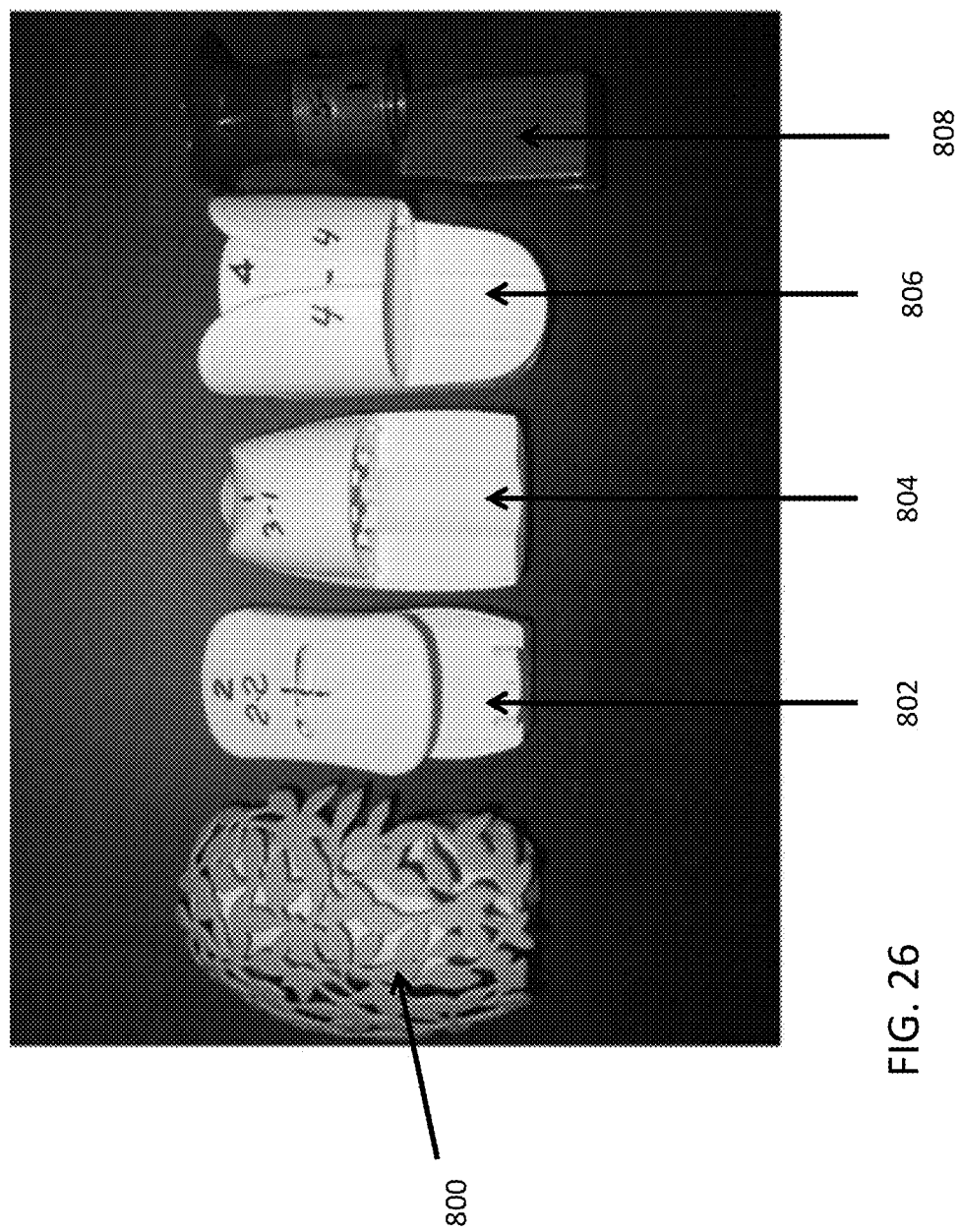
FIG. 26 depicts five volatile material diffusion devices tested during the administration of an Experiment.

An experiment was conducted to measure the overall efficiency of the heater 202 shown in FIG. 16 as compared to heaters in similar devices currently on the market. Referring to FIG. 26, five devices were tested. A first device 800 was similar to the device described herein with respect to FIGS. 1-6 and included the heater 202 as shown and described with respect to FIG. 16 and further included a cover attached thereto, as described above. A second device 802 is a device currently sold by S.C. Johnson & Son, Inc. under the name Glade® Plug-Ins® and detailed in Belongia et al. U.S. Publication No. 2012-0275772. A third device 804 is a device sold by Reckitt Benckiser under the name Air Wick®. A fourth device 806 is a device sold by Procter & Gamble under the name Febreze® Noticeables™ and detailed in U.S. Pat. No. 7,722,807. A fifth device 808 is currently sold by Bath & Body Works, Inc. and is similar to the device detailed in U.S. Pat. No. 6,236,807. Six of each device 800-808 were used for testing and weight loss data for each set of devices was averaged.

A single component proxy formula was used during testing, in particular Tetradecane 99% ($C_{14}H_{30}$). Tetradecane 99% was selected as a proxy because it most closely mimicked the weight loss of a volatile material in the form of a fragrance. In particular, in preliminary testing, Tetradecane 99% exhibited a weight loss and release rate of about 23 milligrams per hour, which falls centrally within the normal weight loss or release rate of most fragrances. More specifically, the normal weight loss or release rate of most fragrances between about 10 and about 40 milligrams per hour. The weight loss refers to the rate at which a volatile material is depleted from the refill. The weight loss for a particular volatile material is the same as the rate at which the volatile material is emitted into the surroundings, which is often referred to as the release rate or output rate.

Refills were filled with 19.8 milliliters of the proxy formula and inserted into each of the devices 800-808. In particular, the refill used for the first and second devices 800, 802 was a refill sold by S.C. Johnson & Son, Inc. and detailed in U.S. Pat. No. 8,197,765. The refills used with the third, fourth, and fifth devices 804, 806, 808 were the refills currently sold with the respective devices. With respect to the fourth device 806, two refills bonded together were filled and inserted into the two compartments of the device 806. With respect to the refills for the devices 800, 802, fresh bottles and wicks were utilized which had not been previously used with another volatile material. The bottles and plugs of the refills for the devices 804, 806, 808 were purchased, drained, rinsed in isopropyl alcohol and allowed to air dry before filling with the proxy formula. The wicks for such refills were placed on absorbent paper towels and allowed to dry for about 96 hours before inserting into the bottles having the proxy formula therein.

The testing facility was an environmentally controlled room maintained at a temperature of 70 degrees Fahrenheit (+/−2° F.) with a humidity of 50% relative humidity (RH) (+/−5%) and an air exchange rate of 22+/−4 air changes per hour. A constant voltage power supply (in the form of AC electrical outlet strips) capable of supplying 120 VAC+/−0.5 volts was used to power the devices 800-808. Other equipment used during the experiment were a calibrated balance capable of a resolution of 0.01 grams, a calibrated multimeter capable of a resolution of at least 0.1 volts, and a calibrated power meter.

Figure 27:
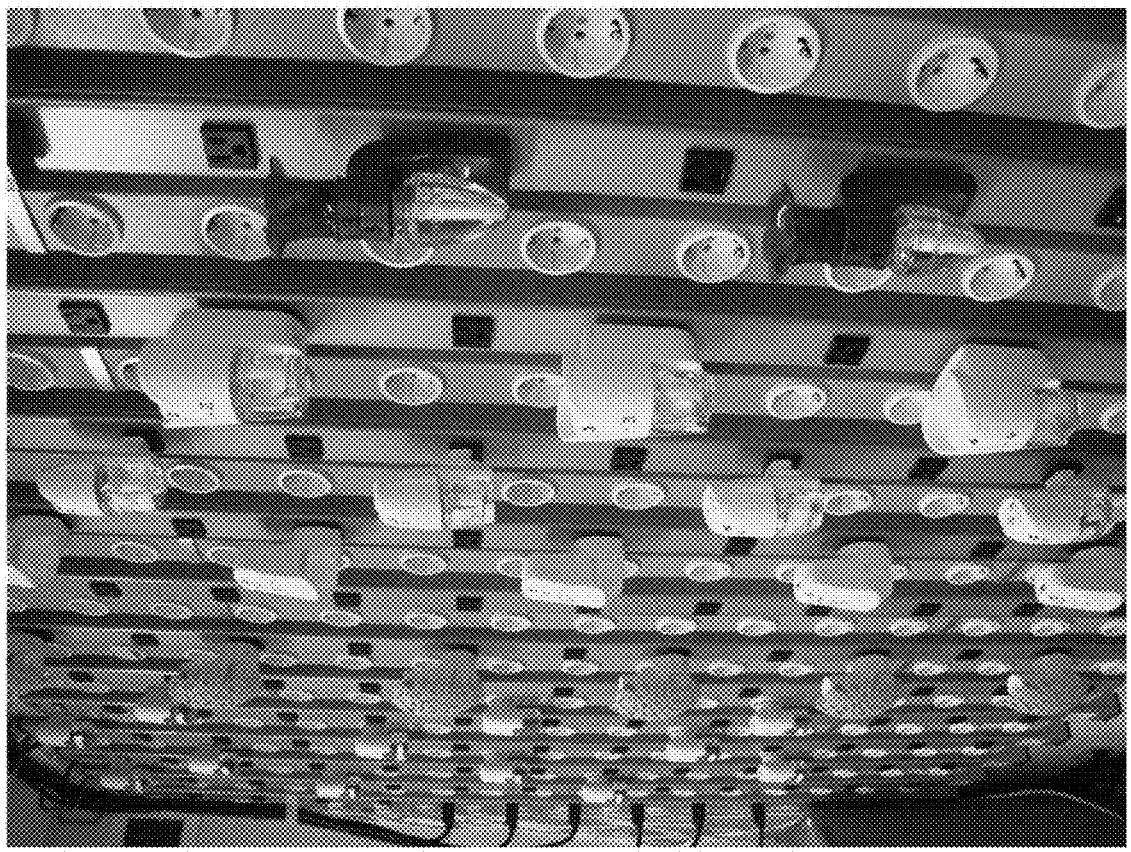
FIG. 27 is a picture depicting the set-up of various devices that were tested during the administration of the Experiment of FIG. 26.

During an initial set-up phase of the Experiment, the initial resistance, current drawn, and power input of each device were measured and recorded. The refills were then installed and a combined weight of each device and refill(s) was measured. After installation of the refill, testing personnel ensured that the wicks were not touching the respective heaters and the devices were installed within outlets, wherein a spacing of at least 6 inches was confirmed between each adjacent device (both horizontally and vertically), as seen in FIG. 27. It was then verified that the temperature, humidity, air exchange rate, and power supply were within acceptable limits. Lastly, for each device including an intensity level switch (all but the fifth device 808, which did not have a means of adjustment), the intensity of the respective device was set to high.

During the testing phase of the Experiment, after the devices were installed within the outlets, weight loss testing was conducted once a day for a total of 10 continuous days. As with the initial weight measurement, the weight of each combined device and refill(s) was measured. A weight loss was calculated for each device using previous and current weight measurements and the weight loss was recorded. An Average Hourly Weight Loss for each device was calculated using weight loss values for Days 3-10 and an Average Overall Hourly Weight Loss for each set of devices was determined by averaging the Average Hourly Weight Loss for each device of that type. During the testing phase, the voltage was checked two times per week using a calibrated voltmeter to ensure it was within proper limits.

In the analysis phase of the Experiment, after the testing was completed and the appropriate data was collected, a device efficiency factor was calculated for each of the devices 800-808 using the equation:

Device Efficiency Factor=Average Overall Hourly Weight Loss/Power

The results of the analysis phase are shown in Table 1 below.

TABLE 1

| Device | Average Overall Hourly Weight Loss (Average overall rate of weight loss (grams/hour) for each set of devices) | Power Input (Watts) |
|---|---|---|
| Device 1: SCJ Infinity PDR 300115059 | 0.026 | 0.886 |
| Device 5: Wallflowers, BBW 006 | 0.022 | 2.241 |
| Device 2: SCJ Billboard, Model Number SCJ168 | 0.012 | 2.406 |
| Device 3: Airwick, ED27 | 0.008 | 1.757 |
| Device 4: Febreze Noticeables, SY982 | 0.027 | 2.200 |

A sample calculation for an efficiency factor for the first device 800 is shown below and the calculated Device Efficiency Factor for each devices is shown in Table 2 below:

Device Efficiency Factor=0.026 g/hour (average overall hourly weight loss)×1000 mg/g/0.886 Watts (power)=29.39

TABLE 2

| Device | Device Efficiency Factor (mg/hr/Watt) |
|---|---|
| Device 1: SCJ Infinity Model Number PDR 300115059, SCJ182 | 29.39 |
| Device 5: Wallflowers, Model Number BBW 006 | 12.30 |
| Device 2: SCJ Billboard, Model Number SCJ168 | 9.71 |
| Device 3: Airwick, Model Number ED27 | 4.98 |
| Device 4: Febreze Noticeables, Model Number SY982 | 4.67 |

In summary, the first device 800 has a significantly higher weight loss/release rate/output rate per unit watt than any of the other devices tested. In fact, the weight loss/release rate/output rate per watt of the first device 800 is more than twice as great as the device with the next highest efficiency, the fifth device 808. Differently said, the amount of power necessary to operate the first device 800 is a fraction of the power necessary for the devices 802, 804, 806, 808 to achieve the same or a greater weight loss/release rate/output rate. The net effect with the first device 800 is energy savings and efficiency.

In illustrative embodiments, a weight loss of at least 0.02 grams per hour is maintained using a power input of less than or equal to 1.5 watts. In alternative illustrative embodiments, a weight loss of at least 0.2 grams per hour is maintained using a power input of less than or equal to about 1.0 watts. In still other illustrative embodiments, a weight loss of at least 0.1 grams per hour is maintained using a power input of less than or equal to about 1.5 watts. In other illustrative embodiments, a weight loss of at least 0.1 grams per hour is maintained using a power input of less than or equal to about 1.0 watts.

In illustrative embodiments, the heater arrangements disclosed herein provide a reduced power consumption of at least about 20% as compared to other similar volatile material dispensers that have an average rate of weight loss that is similar to or less than the average rate of weight loss for dispensers employing the heater arrangements disclosed herein. By a reduced power consumption of at least 20%, it is meant that at least 20% less power is utilized to reach the same average rate of weight loss. In other illustrative embodiments, the heater arrangements provide a reduced power consumption of at least about 30%, at least about 40%, at least about 50%, or at least about 60%, as compared to other similar volatile material dispensers that have an average rate of weight loss that is similar to or less than the average rate of weight loss for dispensers employing the heater arrangements disclosed herein.

In illustrative embodiments, the efficiency factor of one or more of the heaters disclosed herein is greater than or equal to about 13. In other illustrative embodiments, the efficiency factor of one or more of the heaters disclosed herein is greater than or equal to about 15, greater than or equal to about 20, or greater than or equal to about 25.

Alternative Adjustment Mechanisms

Figure 6:
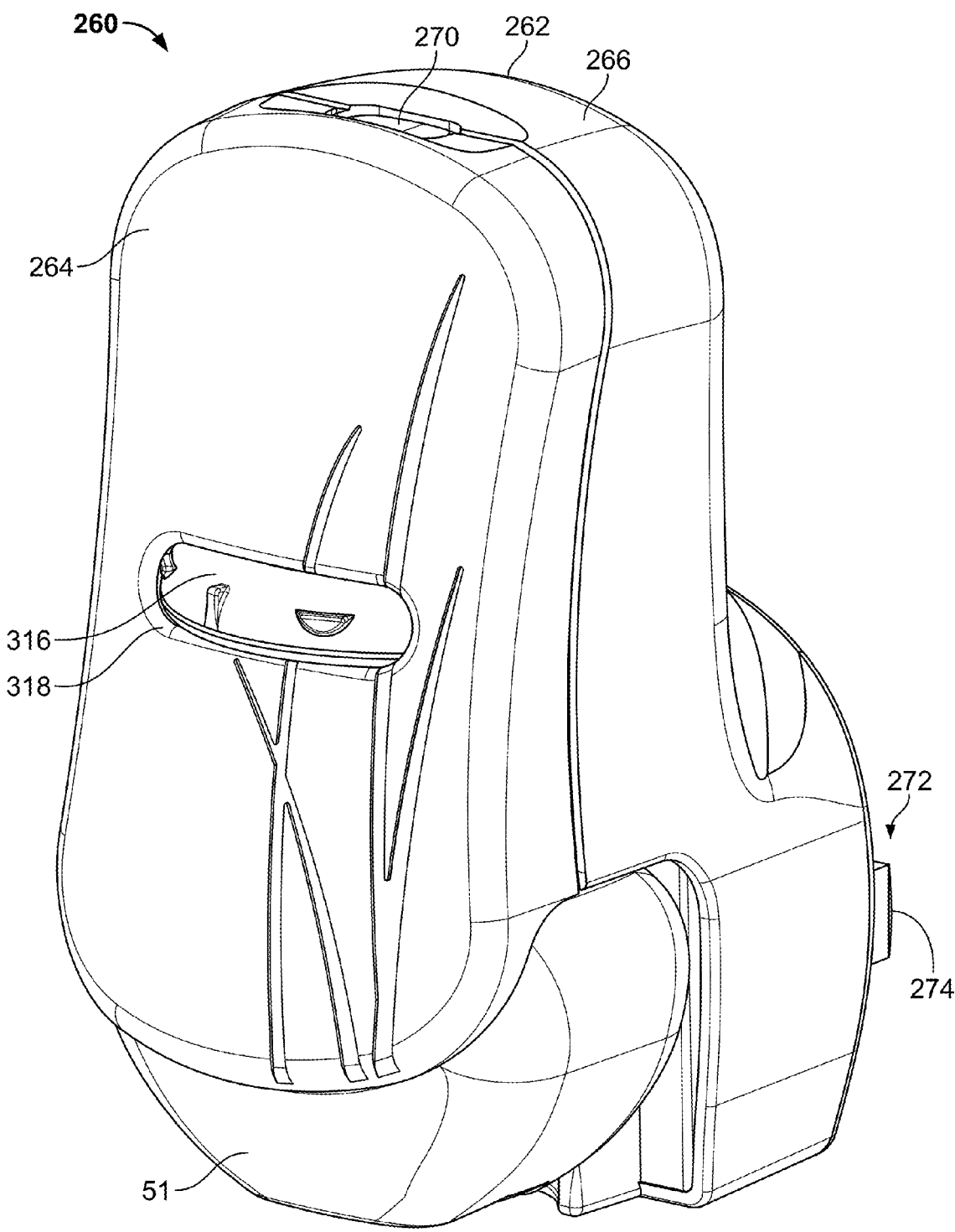
FIG. 6 is a top isometric view of a second embodiment of a volatile material dispenser employing an energy efficient heater arrangement.
Figure 7:
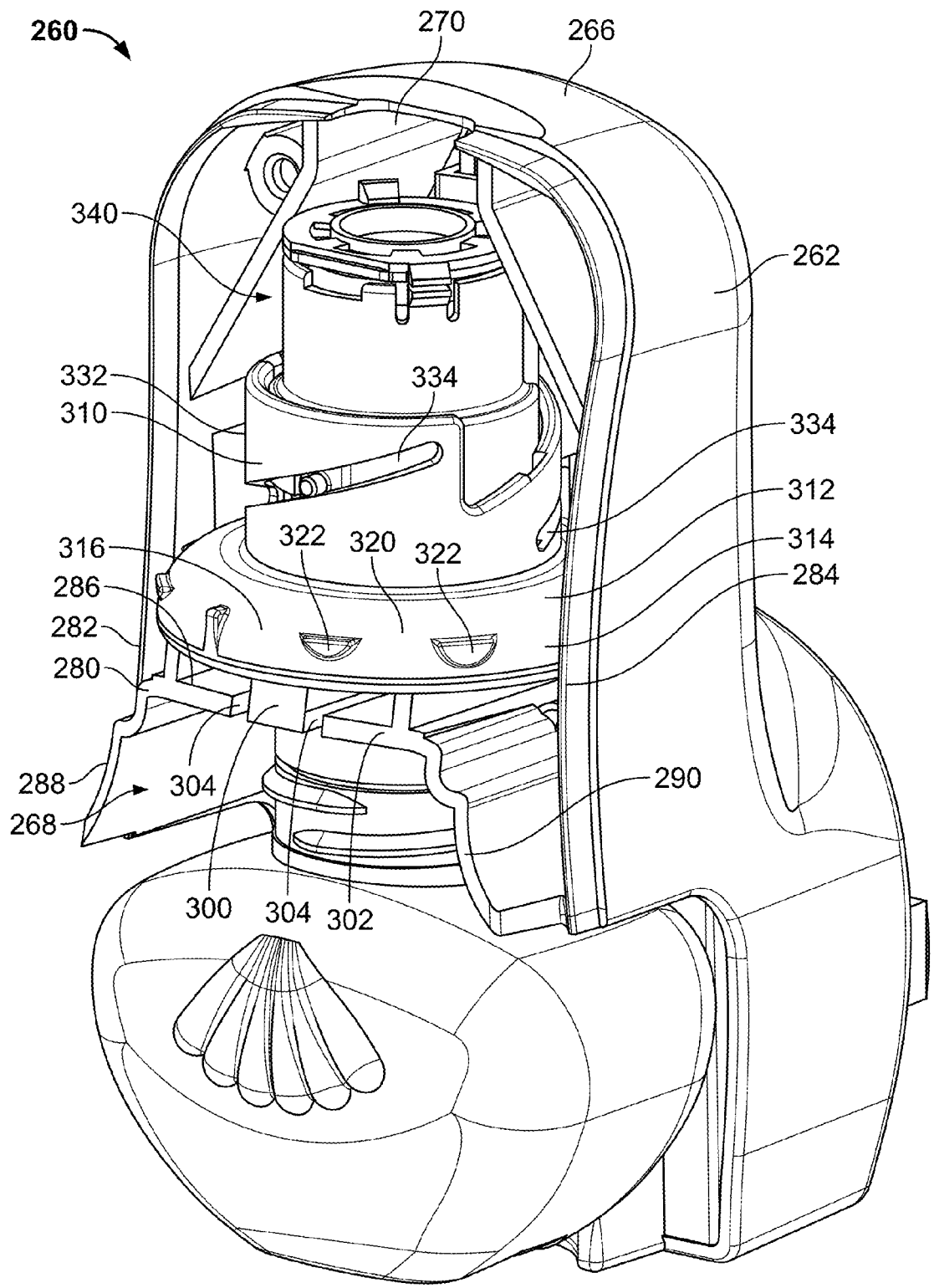
FIG. 7 is a top isometric view of the volatile material dispenser of FIG. 6 with a front portion of a housing removed therefrom to depict an interior cavity of the dispenser.
Figure 8:
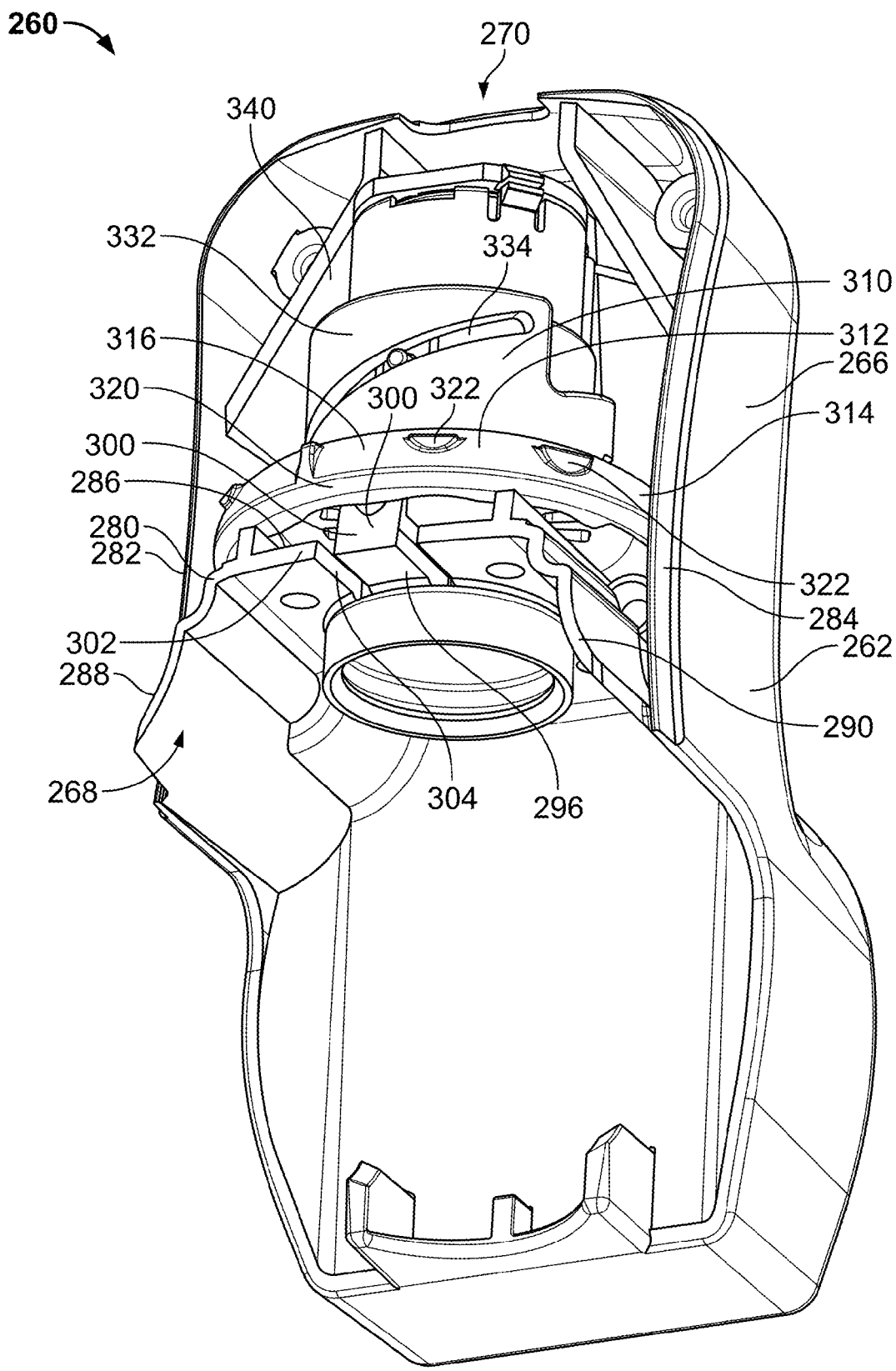
FIG. 8 is a bottom isometric view of the volatile material dispenser of FIG. 6 with a front portion of a housing removed therefrom and illustrating an adjustment mechanism for allowing adjustment of a heater disposed within the volatile material dispenser.
Figure 9:
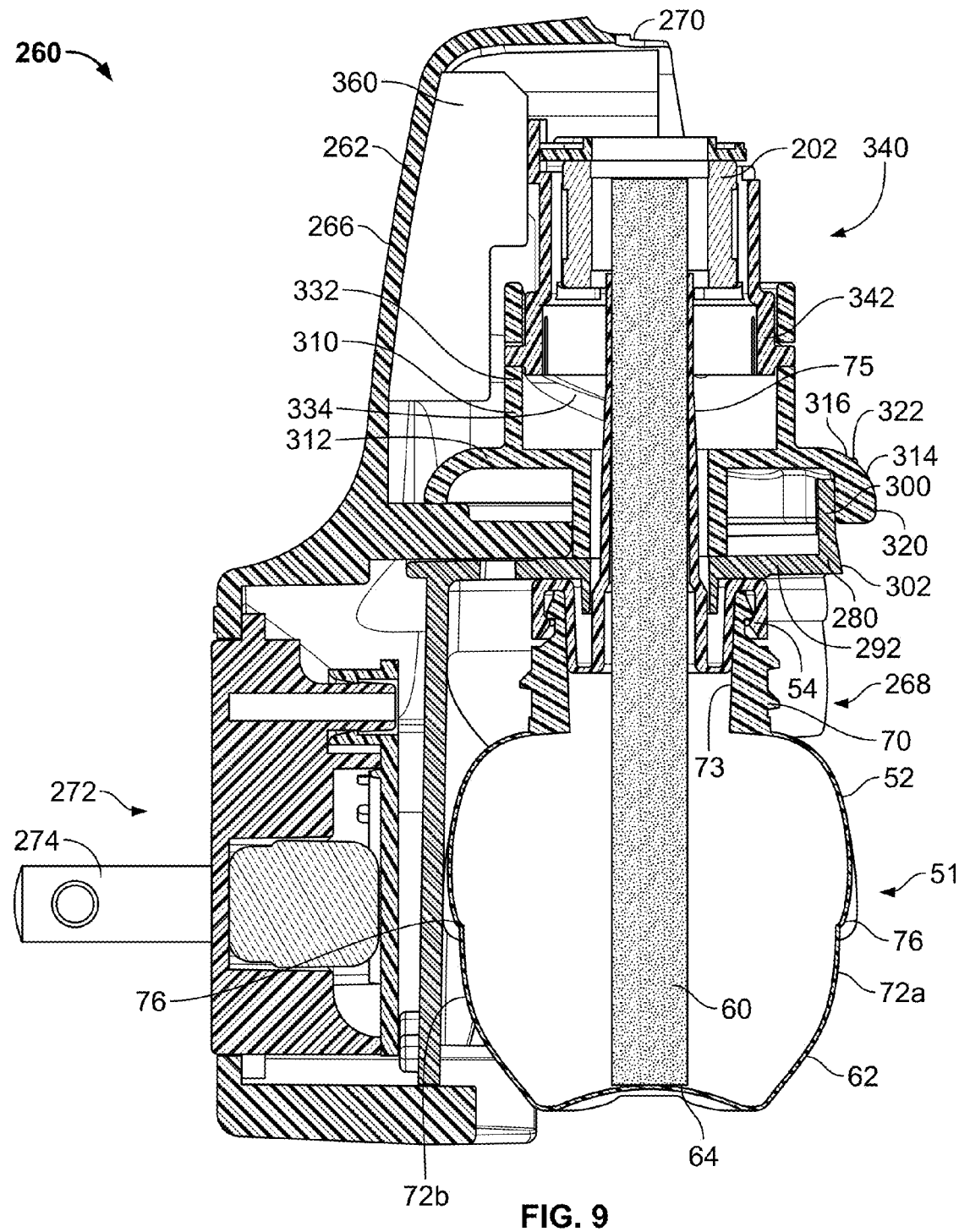
FIG. 9 is a cross-sectional view taken generally along the lines 9-9 of FIG. 7 and generally depicting a heater and the adjustment mechanism.

A second embodiment of a volatile material dispenser 260 is depicted in FIGS. 6-10. The dispenser 260 includes a housing 262 having front and rear portions 264, 266 attached to one another to form an interior chamber or cavity 268 therebetween. The front and rear portions 264, 266 also join to form an aperture 270 at a top of the housing 262 for the emission of volatile material therethrough. The refill 51 is inserted into the housing 262 by inserting the wick 60 upwardly into the chamber 268. Referring to FIGS. 6 and 9, a plug assembly 272 extends from the rear portion 266 of the housing 262 and includes two electrical prongs 274 adapted for insertion into a conventional outlet. While the plug assembly 272 is shown as being a convention plug assembly for the United States, a plug assembly adapted for use in any other country may be utilized. In addition, the plug assembly 272 may include any features known in the art, for example, the plug assembly 272 may be partially or fully rotatable.

Figure 10A:
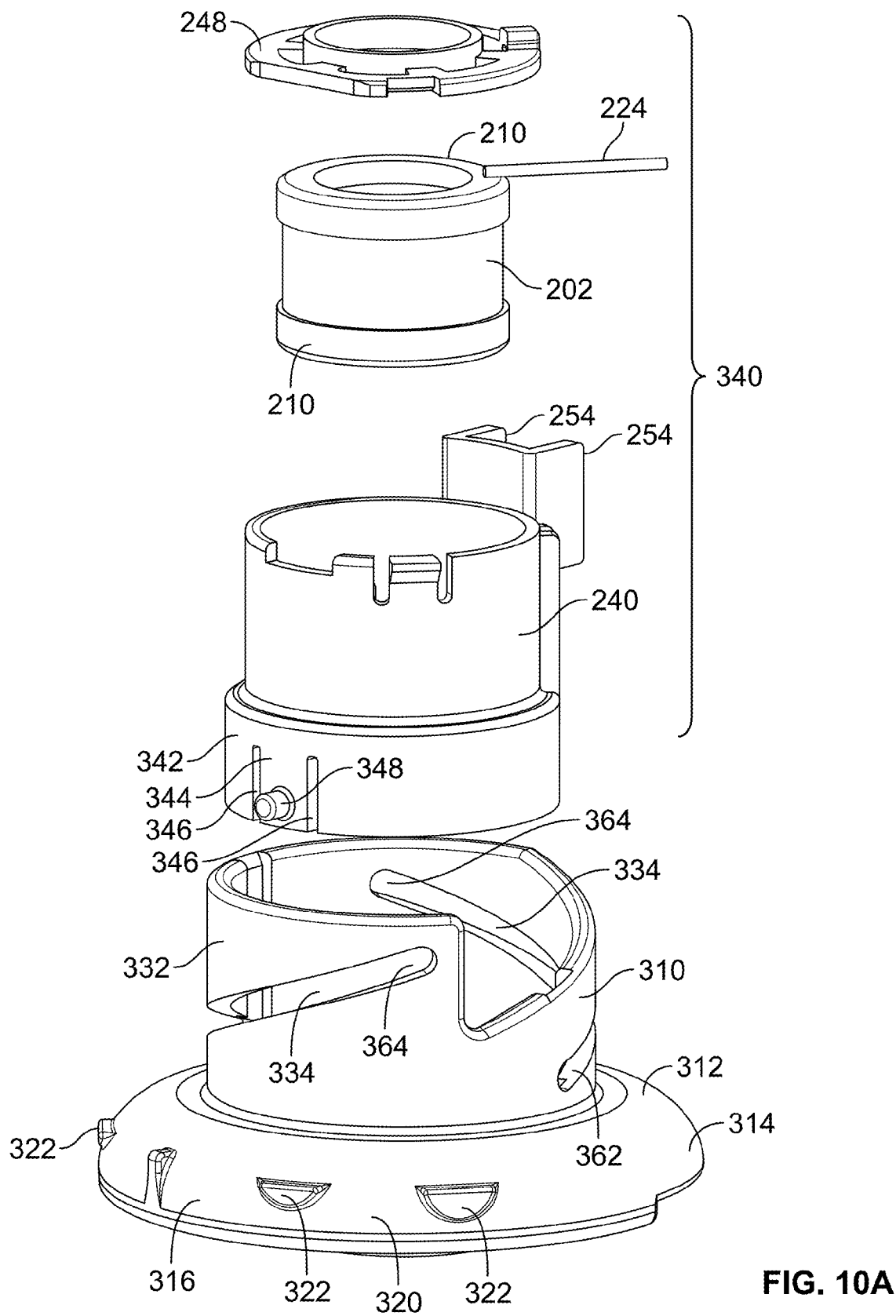
FIG. 10A is an exploded view of the heater and the adjustment mechanism shown in FIGS. 8 and 9.

As best seen in FIGS. 7-9, a stationary support 280 is disposed within the housing 262 and extends between first and second sides 282, 284 of the housing 262. The support 280 includes a generally planar wall 286 and first and second arms 278, 280 extending downwardly and outwardly from opposite ends 292, 294, respectively, of the planar wall 286 to the first and second sides 282, 284. The arms 288, 290 are integral with or otherwise connected to the first and second sides 282, 284 of the housing 262. As best seen in FIG. 10C, the support 280 further includes a flexible tab 300 formed within a front edge 302 of the planar wall 286. In particular, two slots 304 extend inwardly from the front edge 302 to form the tab 300, which flexes about point 306. A projection 308 extends upwardly from a top surface 309 of the tab 300 and includes a curved outer surface 310. A cylindrical channel 311 is formed through the support 280 for positioning of the wick 60, as will be discussed in greater detail below.

An adjustment wheel 312 is attached to the stationary 280 support and includes a base 313 with an outwardly curving wall 314. The wall 314 provides a knob 316 that extends through an aperture 318 in the front portion 264 of the housing 262. An outer surface 320 of the wall 314 may include a plurality of indicia 322 for providing a visual cue of a position of the adjustment wheel 312 (e.g., an intensity level). An inner surface 324 of the wall 314 may include a plurality of notches 326 that are aligned with the indicia 322 and which aid in setting an intensity level for the dispenser 260, as discussed below.

Figure 10B:
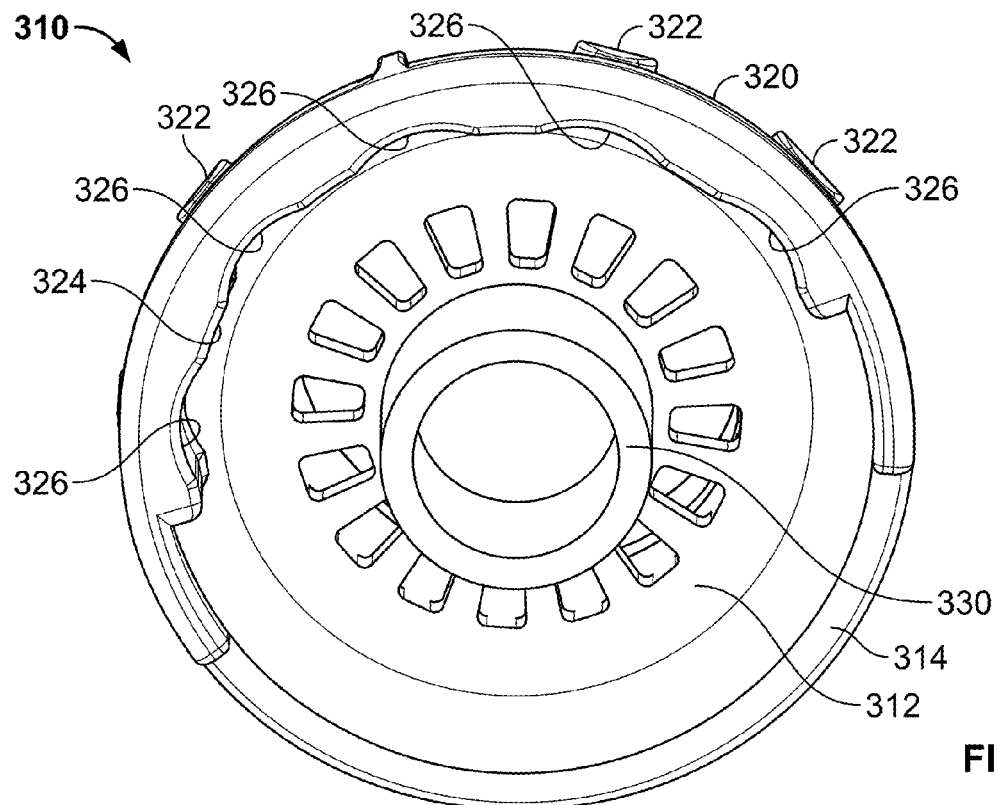
FIG. 10B is a bottom perspective view of an adjustment wheel of the adjustment mechanism of FIGS. 8 and 9.
Figure 10C:
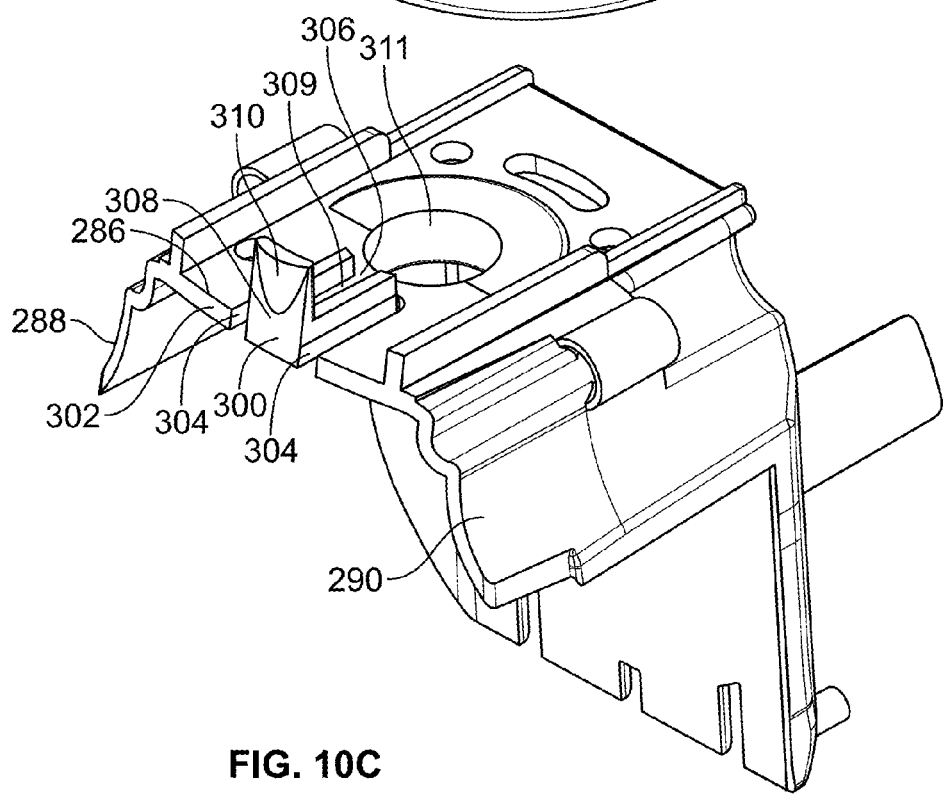
FIG. 10C is a top perspective view of a support of the adjustment mechanism of FIGS. 8 and 9.

As seen in FIG. 10B, the adjustment wheel 312 further includes a first cylindrical wall 330 extending downwardly from the base 313 and disposed inwardly of the wall 314. Referring to FIG. 10A, the adjustment wheel 312 includes a second cylindrical wall 332 extending upwardly from the base 313 and spaced between the first cylindrical wall 30 and the wall 314. Two spiraled apertures 334 are disposed within the second cylindrical wall 332, the function of which will be discussed in greater detail hereinafter.

Still referring to FIG. 10A, the dispenser 260 further includes a heater arrangement 340 similar to the heater arrangement 200 of FIGS. 1-5B. Similar components will therefore be numbered similarly. A cylindrical extension 342 extends downwardly from the container 240 and has a diameter slightly greater than a diameter of the container 240. The extension 342 includes two flexible tabs 344 on opposite sides of the extension 342, wherein each tab 344 is formed by two channels 346 and includes an outwardly extending cylindrical projection 348.

During manufacture, the adjustment wheel 312 is attached to the support 280 by inserting the first cylindrical wall 330 of the adjustment wheel 312 into the cylindrical channel 311 of the support 280. As the adjustment wheel 312 is pressed against the support 280, the projection 308 flexes about the point 306 until the projection 308 is disposed within one of the notches 326 within the inner surface 324 of the wall 314 of the adjustment wheel 312.

The heater arrangement 340 is attached to the adjustment wheel 312 by flexing the tabs 344 inwardly and inserting the extension 342 into the second cylindrical wall 332 of the adjustment wheel 310 such that the projections 348 extend into the spiraled apertures 334. Upon assembling of dispenser 260, the posts 254 extending outwardly from the heater arrangement 340 straddle an anti-rotation wall 360 extending from the housing 262, thereby preventing rotation of the heater arrangement 340.

During operation, a user turns the knob 316 to adjust the intensity of the heater 202. When the knob 316 is set at a lowest intensity, the cylindrical projections 348 are disposed within lower ends 362 of the spiraled apertures 334. As the knob 316 is turned in a clockwise direction, the adjustment wheel 310 is rotated, but the heater arrangement 340 remains stationary due to the anti-rotation wall 360. The cylindrical projections 348 ride up the spiraled apertures 334 toward upper ends 364 of the spiraled apertures 334, thereby causing the heater arrangement 340 to move upwardly and increasing an intensity level. In particular, the heater 202 is disposed around an exposed area of the wick that is larger than in other positions (e.g., the top portion of the wick 60 that does not have the sheath 75). The knob 316 may be turned to move the cylindrical projections 348 within the spiraled apertures 334 to changes the intensity from a lowest intensity (at the lower ends 362 to a highest intensity at upper ends 364).

Figure 11:
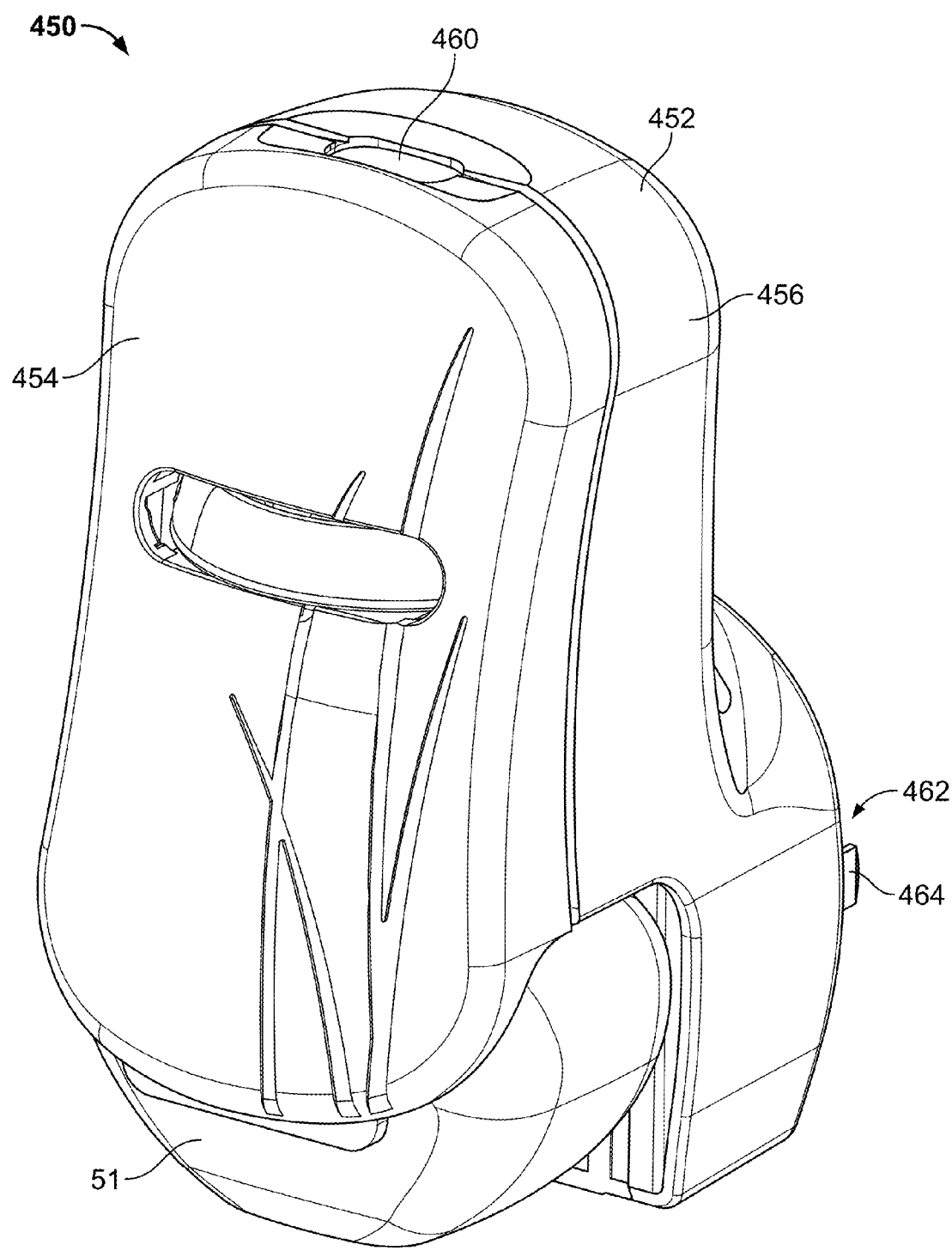
FIG. 11 is a top isometric view of a third embodiment of a volatile material dispenser employing an energy efficient heater arrangement.
Figure 12:
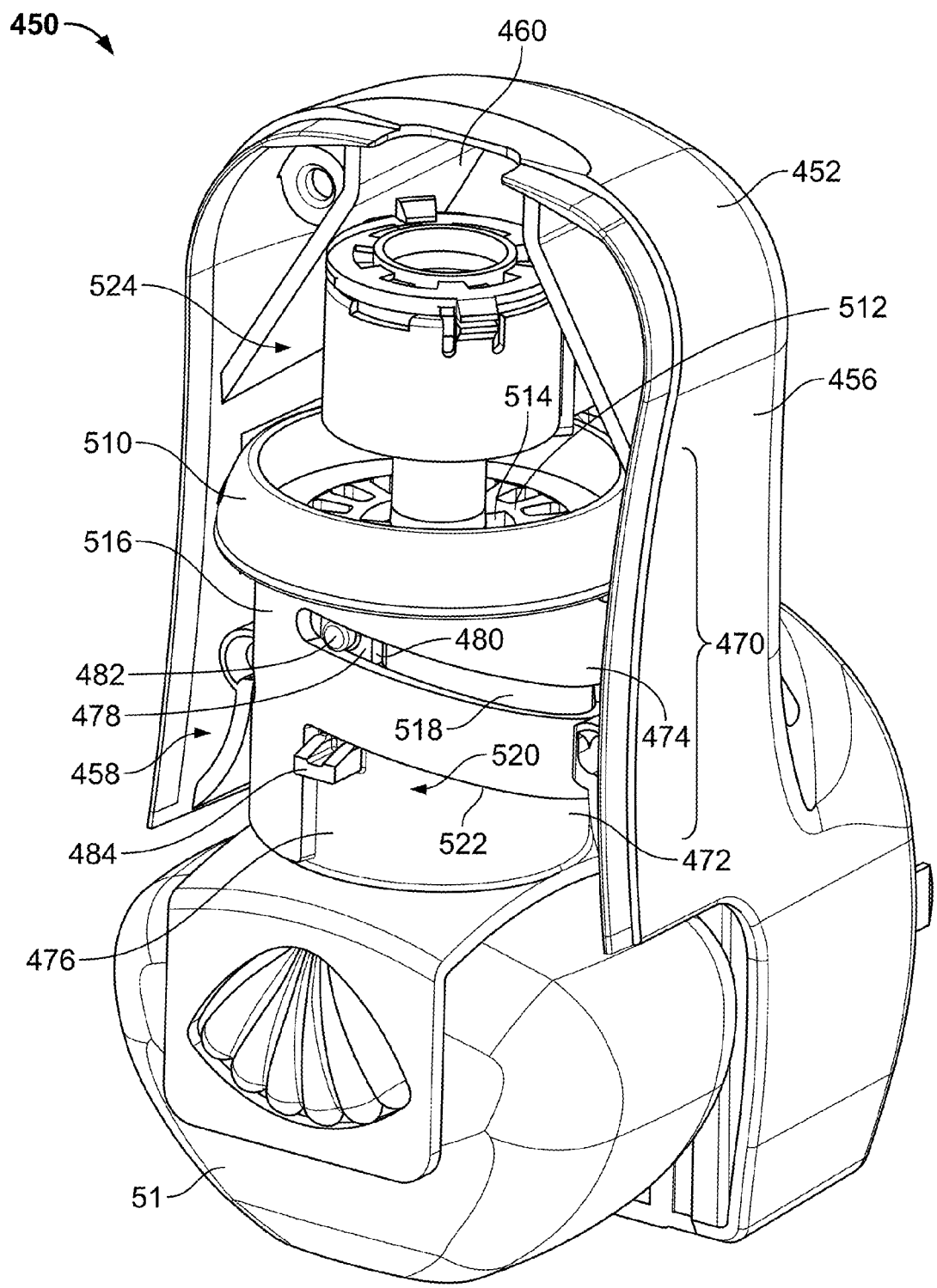
FIG. 12 is a top isometric view of the volatile material dispenser of FIG. 11 with a front portion of a housing removed therefrom to depict an interior cavity of the dispenser.
Figure 13:
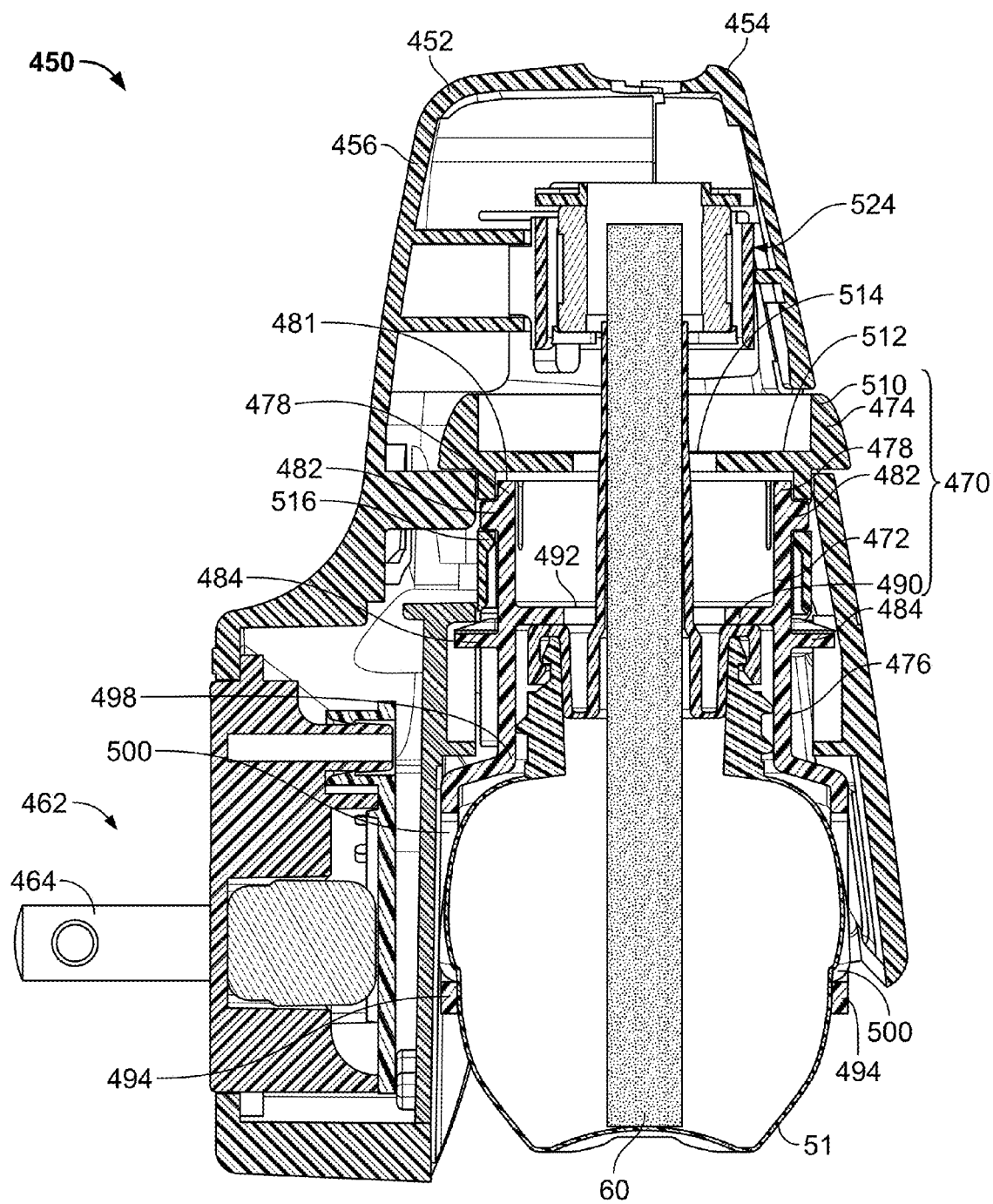
FIG. 13 is a cross-sectional view taken generally along the lines 13-13 of FIG. 11 and depicting a heater and an adjustment mechanism for adjusting a refill disposed within the volatile material dispenser.

A third embodiment of a volatile material dispenser 450 is depicted in FIGS. 11-14. Similar to the previous embodiments, the dispenser 450 includes a housing 452 having front and rear portions 454, 456 attached to one another to form an interior chamber or cavity 458 therebetween. The front and rear portions 454, 456 also join to form an aperture 460 at a top of the housing 452 for the emission of volatile material therethrough. The refill 51 is inserted into the housing 452 by inserting the wick 60 upwardly into the chamber 458. Referring to FIGS. 11 and 13, a plug assembly 462 extends from the rear portion 456 of the housing 452 and includes two electrical prongs 464 adapted for insertion into a conventional outlet. While the plug assembly 462 is shown as being a convention plug assembly for the United States, a plug assembly adapted for use in any other country may be utilized. In addition, the plug assembly 462 may include any features known in the art, for example, the plug assembly 462 may be partially or fully rotatable.

Figure 14:
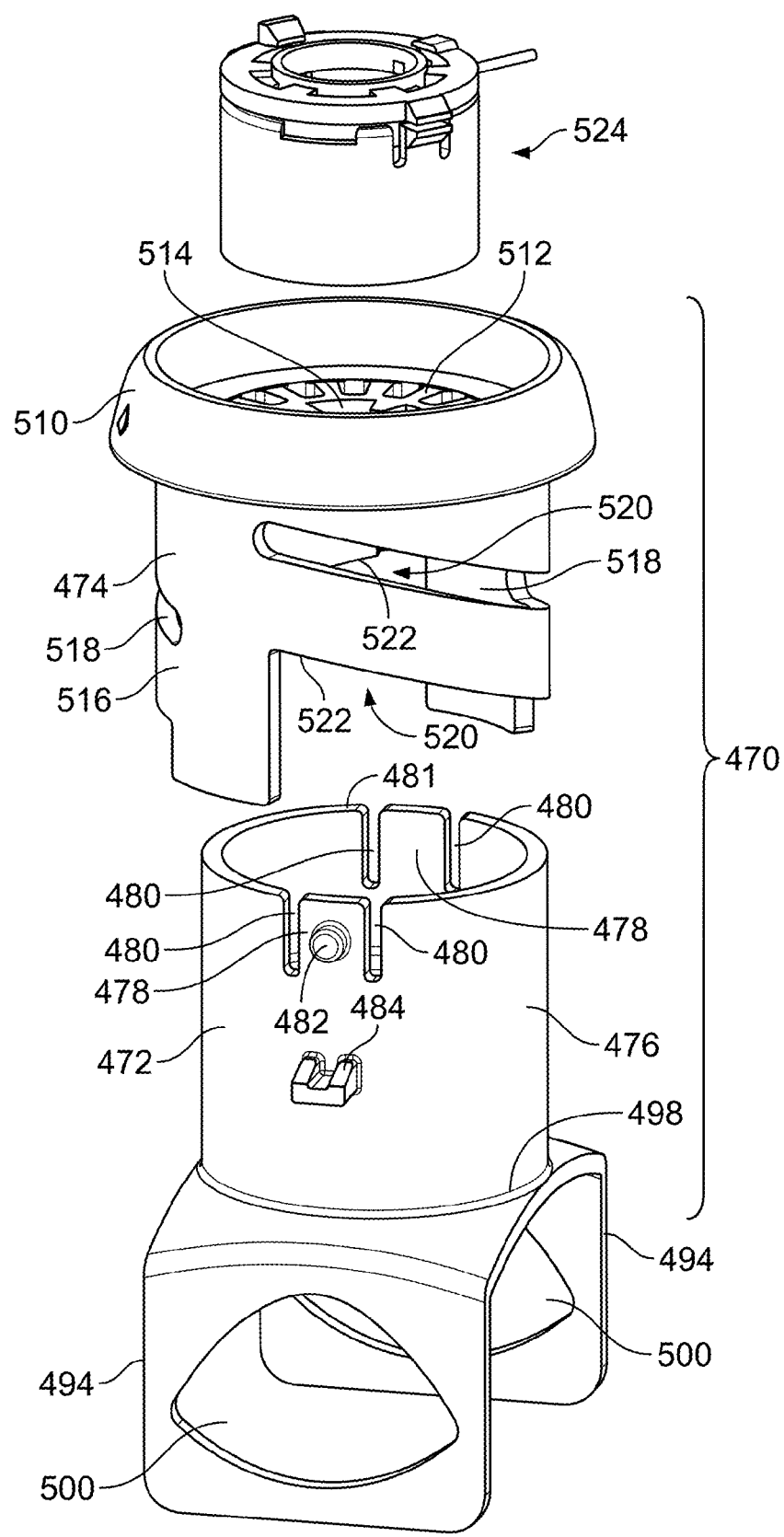

As best seen in FIGS. 12 and 14, the dispenser 450 includes a two-piece adjustment mechanism 470 including a refill holder 472 and an adjustment wheel 474. The refill holder 472 includes a cylinder 476 having first and second tabs 478 formed in an outer top edge 480 of the cylinder 476 at front and rear sides of the cylinder 476. Each tab 478 is formed by slots 481 that allow the tabs 478 to flex. A cylindrical projection 482 extends outwardly from each tab 478. Limiting projections 484 extend outwardly from the cylinder 476 and are spaced below the tabs 478.

Referring next to FIGS. 12, 14, and 15, the refill holder 472 further includes an annular ledge 490 that creates a generally planar surface and includes an aperture 492 therethrough. The wick 60 of the refill 51 may be inserted through the aperture 492, but the annular ledge 490 prevents over-insertion of the refill 51 into the dispenser 50.

The refill holder 472 further includes first and second arms 494 extending outwardly and downwardly from front and rear sides of a lower edge 498 of the cylinder 476. Each arm 494 includes an aperture 500 therethrough. The apertures 500 may be formed in a shape that conforms to the raised portions 76 on the refill 51. The apertures 500 can optionally be any shape that would aid in retaining a refill therein. Still optionally, the arms 494 and/or refill 51 may include any features that aids in attaching and retaining the refill 51 to the arms 494.

Referring to FIGS. 12 and 14, the adjustment wheel 474 includes a knob 510 having a planar wall 512 through a center of and perpendicular to the knob 510 and having an aperture 514 therethrough. The adjustment wheel 474 further includes a cylindrical wall 516 extending downwardly from the knob 510, wherein the cylindrical wall 516 includes two spiraled apertures 518 and two cutouts 520 spaced below the apertures 518 and forming abutment surfaces 522. The abutment surfaces 522 are generally parallel to the spiraled apertures 518. The knob 510 may be turned in a manner similar to the embodiment of FIGS. 7-11, except that the refill 51 is moved up and down, rather than the heater arrangement 200.

The dispenser 450 further includes a heater arrangement 524 that is identical to the heater arrangement 200 of FIGS. 1-6. The heater arrangement is attached to the housing 452 in the manner described with respect to the embodiment of FIGS. 1 and 6 or in any other manner suitable manner. The heater arrangement is spaced above the adjustment wheel 474 While manual adjustment mechanisms are depicted in the drawings and the embodiments detailed herein, an electrical adjustment mechanism may alternatively be used. For example, a multi-position slide switch may be operatively connected to a dropping resistor circuit to vary a temperature of any of the heaters disclosed herein.

Heater Arrangement Enhancements

The heater arrangement features and components of FIGS. 17-25 may be used in combination with the heaters and/or heater arrangements described with respect to the embodiments of FIGS. 1-16 to enhance the efficiency of such heaters and/or heater arrangements.

Figure 17:
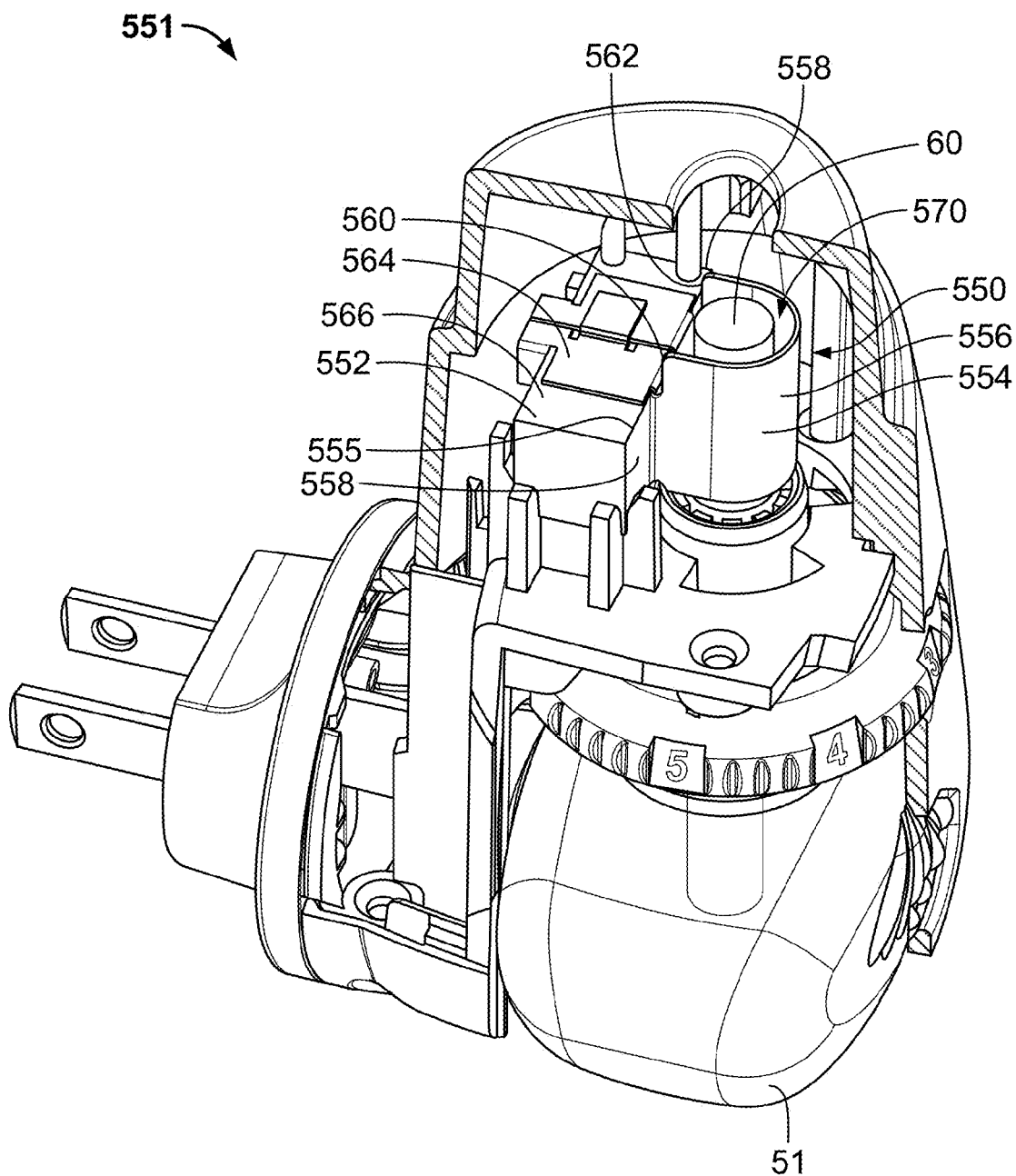

Referring to FIG. 17, a heater arrangement 550 is shown within a volatile material dispenser 551 and may include a typical ceramic heating block 552, which includes one or more resistors (not shown) disposed within the heating block 552, or any heater arrangement as disclosed with respect to FIGS. 1-16. When the resistors are actuated, heat from the resistors is conducted throughout the ceramic heating block 552. The heater arrangement 550 may further include a heat band 554 attached to a surface 555 of the heating block 552 that faces the wick 60 of the refill 51 (when inserted into the dispenser 552). The heat band 554 generally includes a U-shaped wall 556 and a planar wall 558 connected to ends 560, 562 of the U-shaped wall 556. The planar wall 558 is disposed against the surface 555 of the heating block 552. The heat band 554 may be attached to the heating block 552 by a connector 564 that extends generally transverse to the planar wall 558 and over a top surface 566 of the heating block 552. Optionally, the heat band 554 may be attached to the heating block 552 in any suitable manner. Preferably, the heat band 554 is made of a conductive material, such as metal. While the heat band 554 is disclosed as being U-shaped, other arrangements and/or shapes are possible.

With the features of FIG. 17, heat travels through the heat band 554 by conduction, thereby creating a ring of heat around the wick 60. Heat from the ring travels inwardly through the air gap toward the wick 60 through conduction and radiation and gets trapped in a gap 570 between the heat band 554 and the wick 60, thereby increasing the overall temperature in the gap 570 and therefore in the wick 60, creating a uniform application of heat around a circumference of the wick 60, and further increasing volatilization of the volatile material in the wick 60.

Further enhancements are depicted in a heater arrangement 580, as seen in FIGS. 18 and 19, which is incorporated within a volatile material dispenser 582. The heater arrangement 580 may include a resistor 584 extending from a circuit board or other component within the volatile material dispenser 582. The resistor 584 may be encapsulated within a ceramic heating block 586 or may be otherwise encapsulated or spaced from a wick 590. A refill 588 for use with the heater arrangement 580 may be similar to the refill 588 discussed with respect to the first embodiment, except that the refill 588 includes a wick 590 having an opening or cavity 592 for insertion of the resistor 584 and/or the ceramic heating block 586. The wick 590 may further include a sheath 594 disposed around portions of the wick 590 that are in close proximity to the heater arrangement 580.

In a first variation of the heater arrangement 580, as seen in FIG. 18, the resistor 584 and/or ceramic heating block 586 may be suspended within the volatile material dispenser 582 and the cavity 592 in the wick 590 may be created by a hollow cylinder extending through a top surface 596 of the wick 590. During insertion of the refill 588, the wick 590 may be aligned with the resistor 584 and/or ceramic heating block 586 such that the resistor 584 and/or ceramic heating block 586 are disposed within the wick 590 upon full insertion of the refill 588 into the volatile material dispenser 582. In a second variation of the heater arrangement 580, as seen in FIG. 19, the resistor 584 and/or ceramic heating block 586 may extend outwardly from one or more components within the volatile material dispenser 582. The cavity 592 may be formed through a side 600 of the wick 590. During insertion of the refill 588, the cavity 592 formed through the side 600 of the wick 590 may be aligned with the resistor 584 and/or ceramic heating block 586 such that the resistor 584 and/or ceramic heating block 586 are disposed within the wick 590 upon full insertion of the refill 588 into the volatile material dispenser 582.

The features of the heater arrangement 580 of FIGS. 18 and 19 provide increased heater efficiency because the wick 590 is heated uniformly. Also, due to the close proximity of the resistor 584 and/or ceramic heating block 586 to the wick 590 and the fact that the resistor 584 and/or ceramic heating block 586 are disposed within the wick 590, little heat is lost to the surroundings (or other components of the dispenser 580) and the wick 590 is the recipient of most of the emitted heat.

Figure 20:
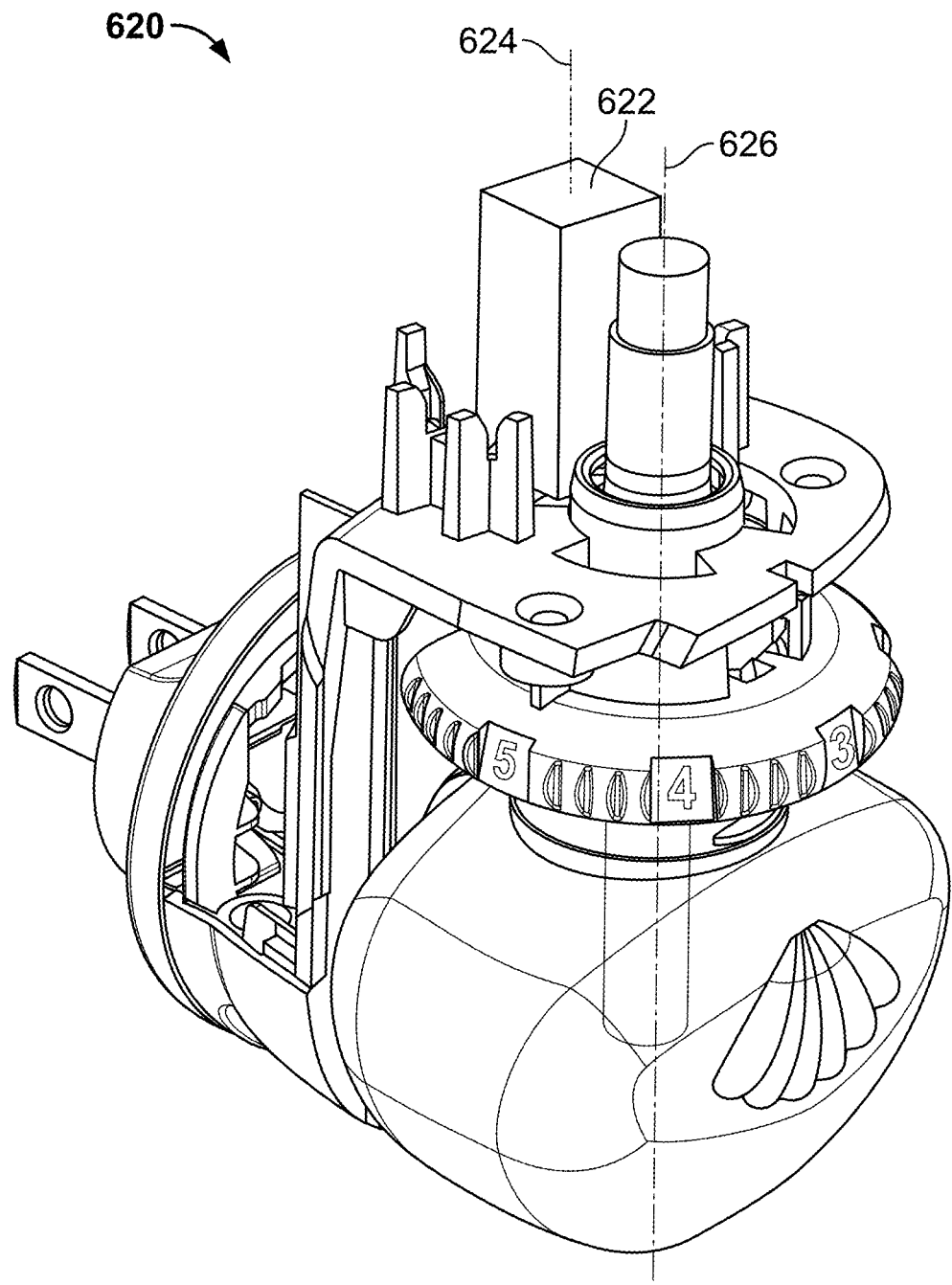

A further heater arrangement 620 is depicted in FIG. 20. The heater arrangement 620 may include a typical ceramic heating block 622, which includes one or more resistors (not shown) disposed within the heating block 622, or any heater arrangement as described with respect to FIGS. 1-16. When the resistors are actuated, heat from the resistors is conducted throughout the ceramic heating block 622. The heating block 622 is different from previous ceramic heating blocks in that it is vertically arranged. In particular, the heating block 622 is a right rectangular prism with three dimensions that are different, wherein the heating block 622 is arranged with a longest of the three dimensions having a longitudinal axis 624 that is parallel to a longitudinal axis 626 of the wick 60. The resistor(s) contained within the heating block 622) may also have a longitudinal axis that is parallel to the longitudinal axis 626 of the wick 60. The vertical arrangement of the heating block 622 allows heat to be directed along a greater length of the wick 60, thereby increasing volatilization of the volatile material therein.

Figure 21:
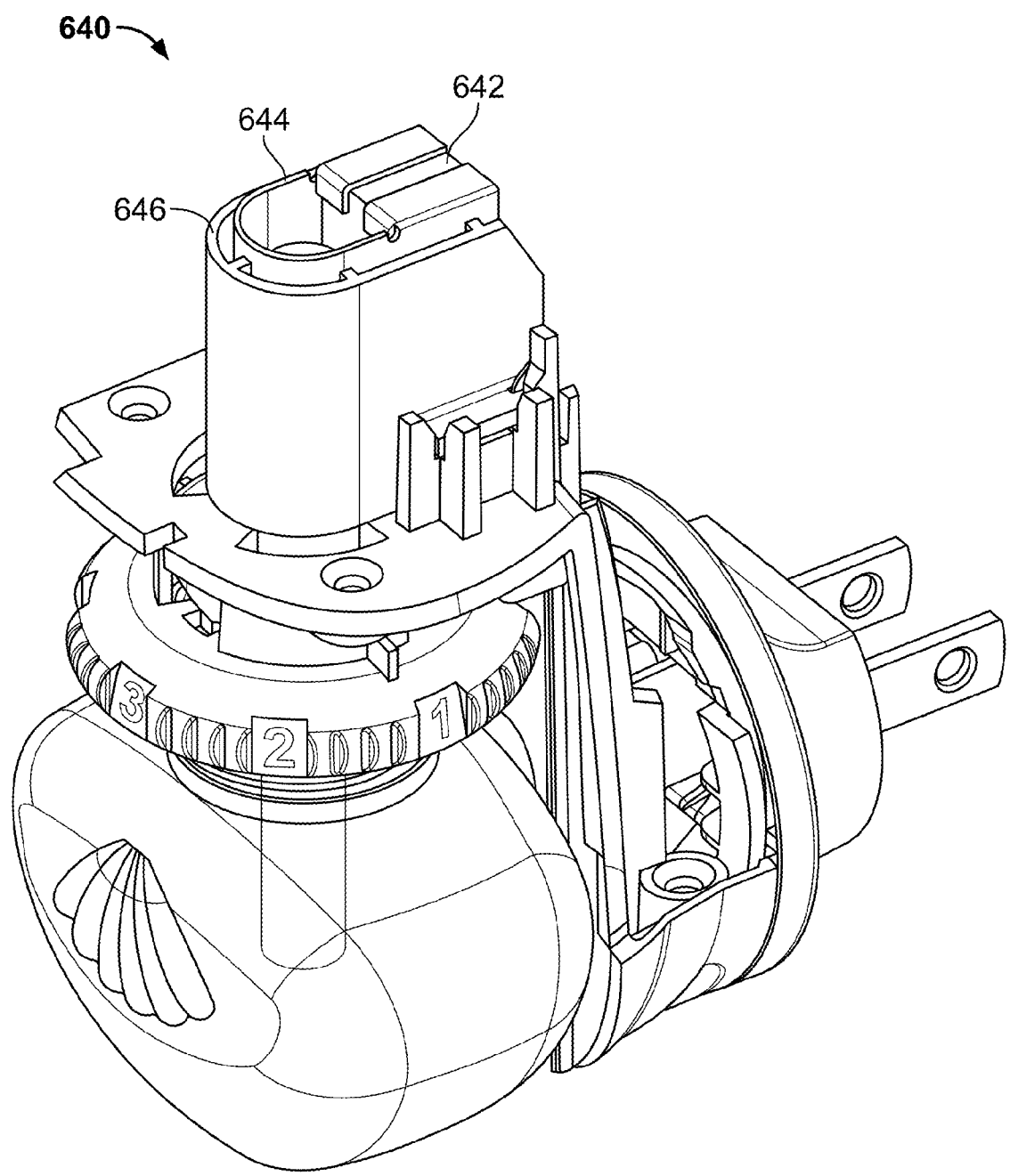

In a heater arrangement 640, as depicted in FIG. 21, both a heat band 644 (as seen in FIG. 17) and a vertical heating block 642 (as seen in FIG. 20) or any heater arrangement as disclosed in FIGS. 1-16, may be utilized to further increase the amount of heat that reaches the wick 60 and increase the overall efficiency of the heater arrangement 640. An insulator 646 may optionally surround the heat band 644 and at least a portion of the heating block 642 to retain heat within the heater arrangement 640.

Figure 22:
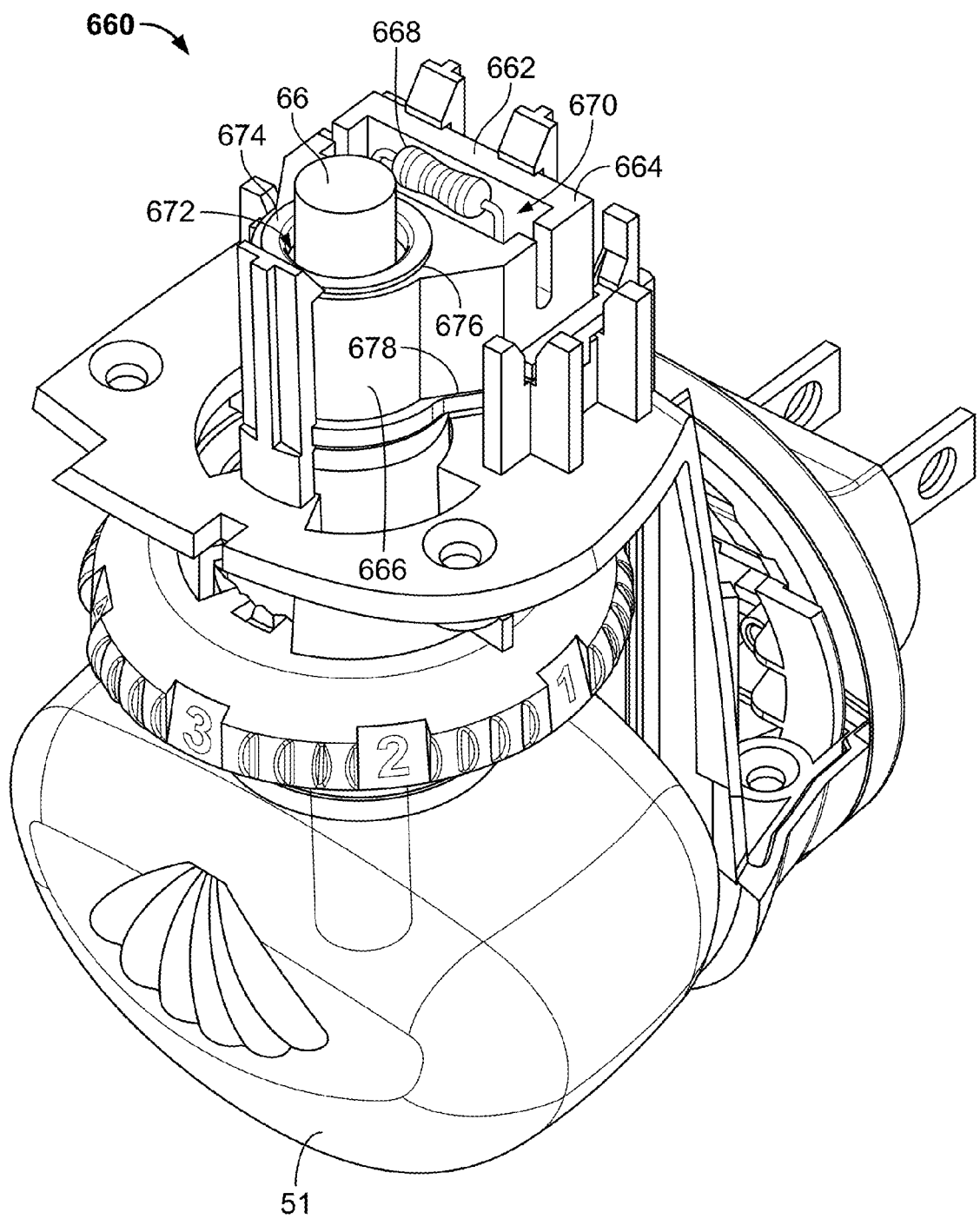

A further heater arrangement 660 is depicted in FIG. 22. The heater arrangement 660 may include a ceramic heating block 662 having a first section 664 with a rectangular cross-section and a second section 666 integral with a generally circular cross-section and extending away from the first section 664. A resistor 668 may be disposed in a cavity 670 disposed within the first section 664 (and may optionally be encapsulated in a ceramic or other conductive material) and a channel 672 may be disposed through the second section 666. Alternatively, any of the heater arrangements disclosed with respect to FIGS. 1-16 may be used. A metal rivet 674 may be attached to top and bottom surfaces 676, 678 of the second section 666 with the rivet 674 extending through and covering a surface of the channel 674. The refill 51 is inserted into the channel 672 of the heating block 662 such that the metal rivet 674 surrounds the wick 60. When the resistor 668 is actuated, heat travels by conduction through the heating block 662. If the heating block 662 does not include the rivet 674, heat travels to all sides of the wick 60, but the heat is lopsided. In particular, a side of the channel 672 closest to the resistor 668 receives quite a bit more heat than an opposite side of the channel 672. When the metal rivet 674 is used, heat reaching the metal rivet 674 is conducted quickly throughout the rivet 674 to more evenly distribute the heat within the rivet 674 and, therefore, to the wick 60.

Figure 23:
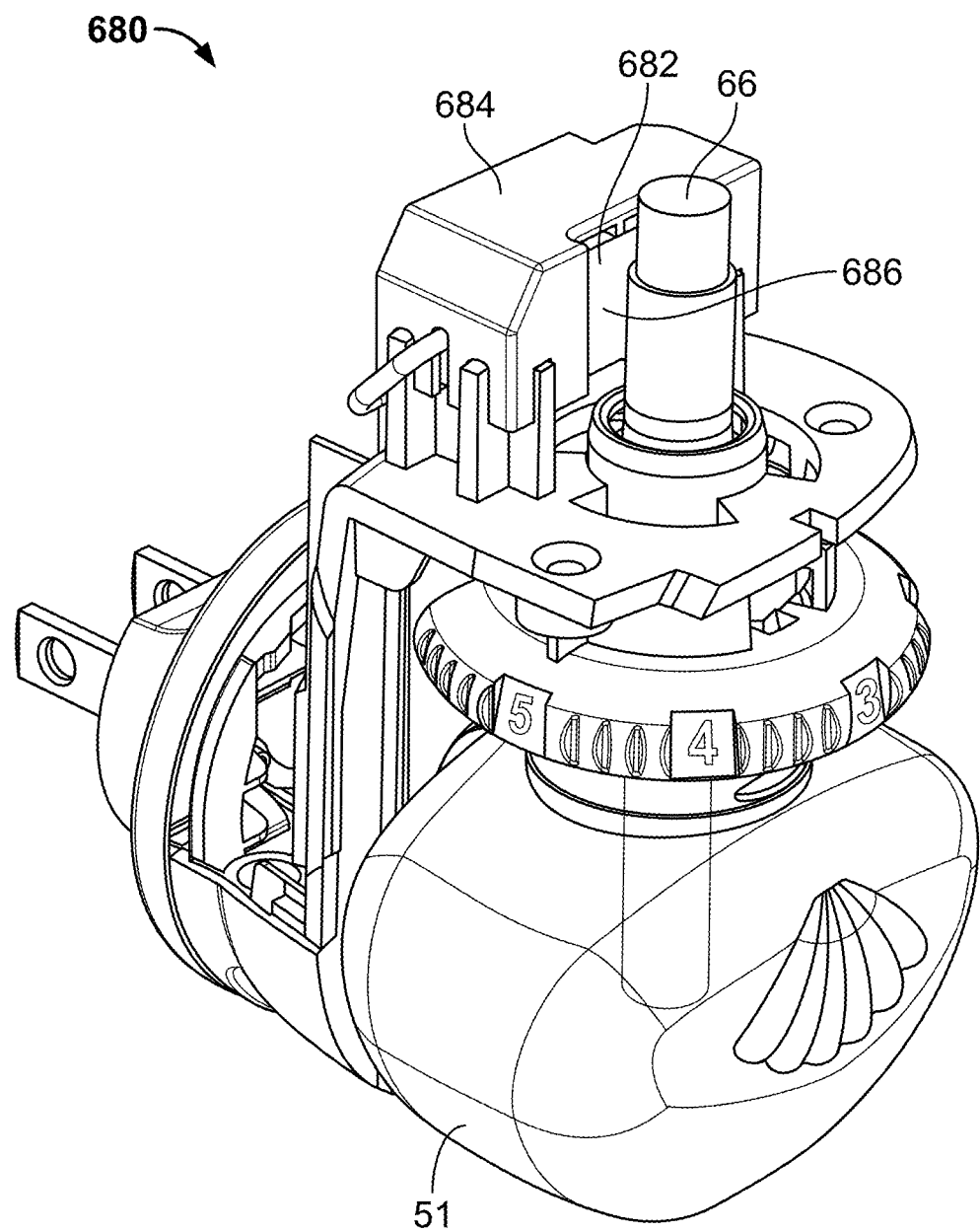

In heater arrangement 680, as seen in FIG. 23, the heater arrangement 680 may include a typical ceramic heating block 682, which includes one or more resistors (not shown), as described in detail above, or any heater arrangement as disclosed in FIG. 15 or 16. An insulator 684 may be disposed over and cover a majority of the heating block 682, wherein the insulator 684 may include a gap 686 where the heating block 682 is not covered. The gap 686 may be aligned with a wick 60 of a refill 51 upon insertion of the refill 51. The insulator 684 prevents migration of heat in directions other than toward the wick 60 and the gap 686 allows migration of heat from the heating block 682 toward the wick 60. As with the other embodiments, the focusing of the heat emitted by the heating block 682 and the decrease in wasted heat (moving in other directions except toward the wick 60) is minimized.

Figure 24:
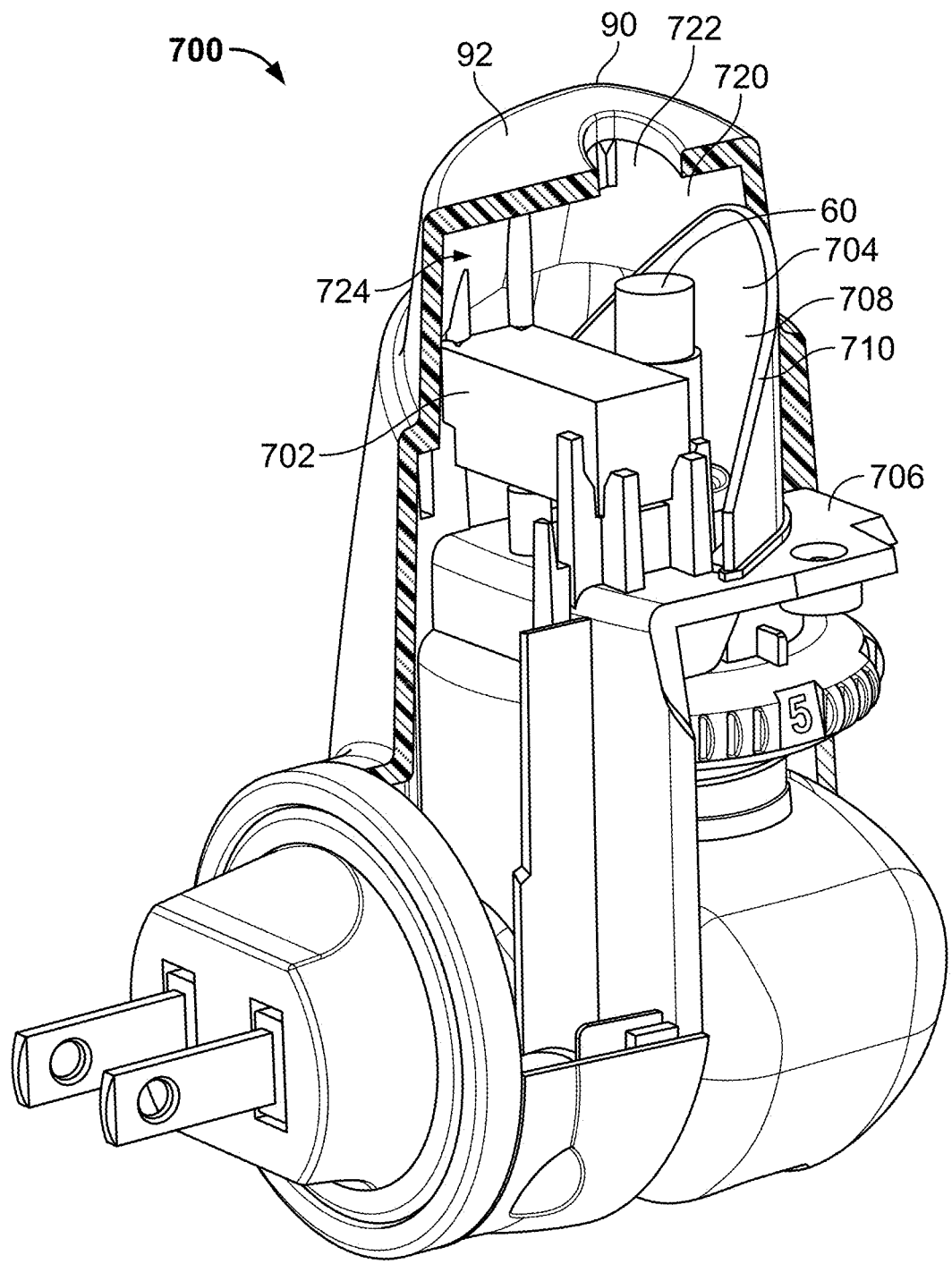

A heater arrangement 700, as shown in FIG. 24, may include a typical ceramic heating block 702, which includes one or more resistors (not shown), as described in detail above, or any of the heater arrangements as disclosed with respect to FIGS>1-16. The heater arrangement 700 may further include a heat reflector or insulator 704 disposed opposite the heating block 702. The reflector or insulator 704 may extend from a generally planar surface 706 and having a curved wall 708 with a generally elliptical top edge 710. The top edge 710 of the wall may curve upwardly as it moves away from the heating block 702 such that a highest point of the wall 708 is disposed opposite the heating block 702.

When a refill 51 is disposed within the heater arrangement 700 of FIG. 24, some of the heat emitted by the heating block 702 hits the wick 60, but a lot of the heat passes the wick 60. If a reflector 704 is used, heat that passes the wick 60 and hits the reflector 704 is reflected back at the wick 60. If an insulator 704 is used, heat that passes the wick 60 is caught within the insulator 704 and is caused to aggregate within the insulator 704, such that when enough heat is caught within the insulator 704, the heat is pushed toward the wick 60. While the reflector or insulator 704 is shown as having a specific configuration, the configuration may be altered without departing from the scope of the present invention. For example, the reflector or insulator 704 may be a full half-circle or may extend from the heating block 702. Various other configurations are possible. In addition, any number of reflectors and/or insulators may be utilized. If a reflector is used, the reflector may be comprised of one or more reflective materials, including but not limited to, aluminum foil or any other suitable thermally reflective material. If an insulator is used, the insulator may be comprised of one or more insulator materials, including but not limited to polystyrene, fiberglass, rigid ceramic, polypropylene, fiberglass, or any other suitable insulator material or materials. A flexible and formable material may also be used as an insulator, for example, a ceramic tape.

As seen in FIG. 24, the reflector or insulator 704 may be used in combination with a reflector 720 mounted on an interior surface 722 of the front and/or rear portions 90, 92 of the housing 56. Any portion or an entire interior surface 722 may include the reflector 704 such that heat emitted by the heating block 702 may continue to bounce around a chamber 724 until it is absorbed by the wick 60. Although some of the heat may be lost, more heat than in conventional dispensers will be absorbed by the wick 60, thereby creating a more efficient heater arrangement 700.

Figure 25:
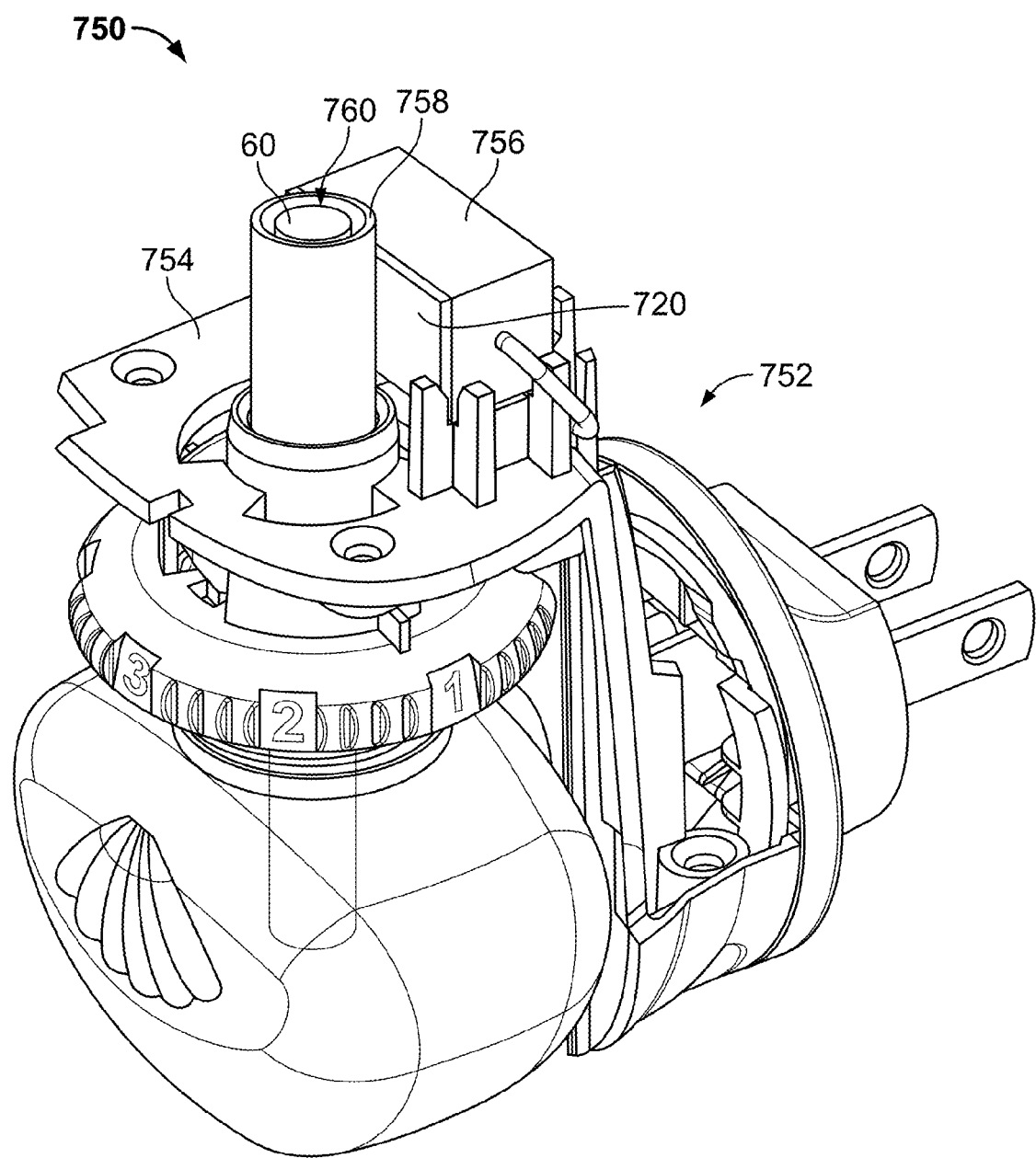

Another heater arrangement 750 is depicted in FIG. 25. A volatile material dispenser 752 in which the heater arrangement 750 is disposed may include a platform 754 for holding a heating block 756 similar to any of the heating blocks or heater arrangement described herein. Alternatively, the heating block 756 may be replaced by any suitable heater. The heater arrangement 750 may further include an aluminum cylinder 758 integral with or otherwise attached or connected to the platform 754 or other component of the dispenser 752. A channel 760 extends through the aluminum cylinder 758 and may be adapted for insertion of a wick 60 therethrough. The heating block 756 (or other heater) may be adjacent, spaced from, or in direct contact with the aluminum cylinder 758. When the heating block 756 is actuated, heat produced travels by conduction through the aluminum cylinder 758, thereby forming a ring of heat around the wick 60. The closer the heating block 756 is to the aluminum cylinder 758 (directly connected to), the more efficient the heat transfer. In this manner, heat is applied consistently to an annular surface of the wick 60.

Although the heater arrangements herein are described as being utilized with dispensers that utilize refills with plug-in scented oils, the heater arrangements may be utilized for any electrical dispenser from which any type of volatile material is dispensed out of any type of refill by way of a heater. Optionally, a dispenser employing any of the heater arrangement disclosed herein may further include one or more heaters and/or additional devices for dispensing the volatile material, for example, one or more of a fan, a piezoelectric element, and/or other components disposed in a housing thereof to help facilitate the release of volatile material. Still further, one or more of the same or different heater arrangements as disclosed herein may be employed within the same volatile material dispenser.

One skilled in the art should understand that variations of the heater arrangements as disclosed herein may be utilized. For example, any number of the features of any of the embodiments herein may be combined to further increase heater efficiency and decrease overall power consumption.

The heater arrangements disclosed herein more effectively and efficiently focus heat around a circumference of the wick and along a greater length of the wick. The heater arrangements disclosed herein may include only a heater or may include any number of other components, as described in detail above.

Any of the embodiments described herein may be modified to include any of the structures or methodologies disclosed in connection with other embodiments.

Further, although directional terminology, such as front, back, top, bottom, upper, lower, etc. may be used throughout the present specification, it should be understood that such terms are not limiting and are only utilized herein to convey the orientation of different elements with respect to one another.

All documents cited in the Detailed Description are, in relevant part, incorporated herein by reference; the citation of any document is not to be construed as an admission that it is prior art with respect to the present disclosure.

INDUSTRIAL APPLICABILITY

The present invention provides energy efficient heater arrangements for volatile material dispensers. The heater arrangements provide a weight loss/release rate/output rate that is the same or greater than previous devices at a lower power consumption. In this manner, less energy is used to power devices including the disclosed energy efficient heater arrangements.

Numerous modifications to the present disclosure will be apparent to those skilled in the art in view of the foregoing description. Accordingly, this description is to be construed as illustrative only and is presented for the purpose of enabling those skilled in the art to make and use the embodiments of the disclosure and to teach the best mode of carrying out same. The exclusive rights to all modifications which come within the scope of the appended claims are reserved.

We claim:

1. A volatile material dispenser, the dispenser including:
   a housing having at least one wall and a cavity disposed within the housing;
   a refill having a volatile material therein and a wick in contact with the volatile material and extending out of the refill; and
   a heater arrangement disposed within the cavity and surrounding the wick when the refill is inserted into the dispenser;
   wherein the heater arrangement operates at a power of less than or equal to about 1.5 watts to achieve an average weight loss of at least 0.01 grams per hour; and wherein the heater arrangement is in the form of a hollow ceramic cylinder with a resistive coating that is deposited on the hollow ceramic cylinder and a spiral pattern is cut into the resistive coating to create a desired resistance value for the heater.

2. The volatile material dispenser of claim 1, wherein the heater arrangement is in the form of a hollow cylindrical heater surrounding the wick and having an air gap of between about 0.5 millimeters and about 2.5 millimeters between an inner surface of the heater and an outer surface of the wick.

3. The volatile material dispenser of claim 1, wherein the heater arrangement is in the form of a hollow cylindrical heater disposed within a hollow container forming a channel through which the wick is inserted.

4. The volatile material dispenser of claim 3, wherein an inner wall of the hollow container forming the channel is spaced between about 0.5 millimeters and about 2.5 millimeters from the wick when the wick is inserted into the channel.

5. The volatile material dispenser of claim 1, wherein connectors or terminals extend from the hollow ceramic cylinder to an electrical component of the dispenser to provide electrical power to the heater.

6. The volatile material dispenser of claim 1, wherein the hollow ceramic cylinder is coated in an electrically insulating coating.

7. The volatile material dispenser of claim 1, wherein the heater with resistive coating has a nominal resistance of between about 14 Kohms and about 16 Kohms with a 5% tolerance and a maximum rated power of 3 Watts.

8. A volatile material dispenser, the dispenser including:
   a housing having at least one wall and a cavity disposed within the housing;
   a refill having a volatile material therein and a wick in contact with the volatile material and extending out of the refill; and
   a heater arrangement disposed within the cavity and disposed adjacent the wick when the refill is inserted into the dispenser, wherein the heater arrangement has a device efficiency factor of greater than or equal to about 13 milligrams per hour per watt; wherein the device efficiency factor is defined as an average overall hourly weight loss divided by the heater arrangement input power; and wherein the heater arrangement is in the form of a hollow ceramic cylinder with a resistive coating that is deposited on the hollow ceramic cylinder and a spiral pattern is cut into the resistive coating to create a desired resistance value for the heater.

9. The volatile material dispenser of claim 8, wherein the device efficiency factor of the heater arrangement is greater than or equal to about 20 milligrams per hour per watt.

10. The volatile material dispenser of claim 8, wherein the device efficiency factor of the heater arrangement is greater than or equal to about 25 milligrams per hour per watt.

11. The volatile material dispenser of claim 8, wherein the heater arrangement is in the form of a hollow cylindrical heater surrounding the wick and having an air gap of between about 0.5 millimeters and about 2.5 millimeters between an inner surface of the heater and an outer surface of the wick.

12. The volatile material dispenser of claim 8, wherein the heater arrangement is in the form of a hollow cylindrical heater disposed within a hollow container forming a channel through which the wick is inserted.

13. The volatile material dispenser of claim 8, wherein the heater arrangement operates at a power of less than or equal to about 1.5 watts to achieve an average weight loss of at least 0.01 grams per hour.

14. A method of emitting a volatile material, the method including the steps of:
   a. providing a volatile material dispenser having least one wall and a cavity disposed within the housing, wherein the housing accommodates a refill having a volatile material and a wick in contact with the volatile material and extending out of the refill;
   b. positioning a heater arrangement within the dispenser, wherein the heater arrangement is configured to reduce the power necessary to operate the dispenser, wherein the heater arrangement includes a heating block positioned adjacent the wick and a heat band having first and second ends, wherein the first and second ends of the heat band are coupled to at least one surface of the heating block; and
   c. operating the heater arrangement at a power of less than or equal to about 1.5 watts to achieve an average weight loss of at least 0.1 grams per hour.

15. The method of claim 14, further including the step of providing the heater arrangement in the form of the heat band extends around the wick forming an air gap between an inner surface of the heat band and an outer surface of the wick, wherein the air gap is between about 0.5 millimeters and about 2.5 millimeters, and the heat band creates a uniform application of heat around a circumference of the wick.

16. The method of claim 14, further including the step of providing the heater arrangement in the form of an insulator positioned to surround the heat band and at least a portion of the heating block, wherein the insulator retains heat within the heater arrangement.

* * * * *